United States Patent
Nikolski et al.

(10) Patent No.: US 10,350,425 B2
(45) Date of Patent: *Jul. 16, 2019

(54) TACHYARRHYTHMIA INDUCTION BY AN EXTRA-CARDIOVASCULAR IMPLANTABLE CARDIOVERTER DEFIBRILLATOR

(71) Applicant: Medtronic, Inc., Minneapolis, MN (US)

(72) Inventors: Vladimir P. Nikolski, Blaine, MN (US); David A. Anderson, Stanchfield, MN (US); Mark T. Marshall, Forest Lake, MN (US); Robert T. Sawchuk, Roseville, MN (US); Amy E. Thompson-Nauman, Ham Lake, MN (US); John D. Wahlstrand, Shoreview, MN (US); Gregory A. Younker, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/051,841

(22) Filed: Aug. 1, 2018

(65) Prior Publication Data
US 2018/0339161 A1 Nov. 29, 2018

Related U.S. Application Data

(63) Continuation of application No. 15/367,448, filed on Dec. 2, 2016, now Pat. No. 10,046,168.
(Continued)

(51) Int. Cl.
*A61N 1/39* (2006.01)
*A61N 1/38* (2006.01)
*A61N 1/378* (2006.01)

(52) U.S. Cl.
CPC .......... *A61N 1/385* (2013.01); *A61N 1/3925* (2013.01); *A61N 1/3956* (2013.01);
(Continued)

(58) Field of Classification Search
CPC ..... A61N 1/385; A61N 1/3962; A61N 1/3987
See application file for complete search history.

(56) References Cited

U.S. PATENT DOCUMENTS

| 5,184,616 A | 2/1993 | Weiss |
| 5,215,083 A | 6/1993 | Drane |

(Continued)

FOREIGN PATENT DOCUMENTS

| WO | 2004047919 A1 | 6/2004 |
| WO | 2015164442 A1 | 10/2015 |

OTHER PUBLICATIONS (PCT/US2016/064571) PCT Notification of Transmittal of the International Search Report and the Written Opinion of the International Searching Authority, dated Feb. 17, 2017, 12 pages.

*Primary Examiner* — William J Levicky

(57) ABSTRACT

An extra-cardiovascular implantable cardioverter defibrillator (ICD) is configured to induce a tachyarrhythmia by charging a high voltage capacitor to a voltage amplitude and delivering a series of pulses to a patient's heart by discharging the capacitor via an extra-cardiovascular electrode vector. Delivering the series of pulses includes recharging the high-voltage capacitor during an inter-pulse interval between consecutive pulses of the series of pulses.

22 Claims, 16 Drawing Sheets

Related U.S. Application Data

(60) Provisional application No. 62/262,500, filed on Dec. 3, 2015.

(52) U.S. Cl.
CPC ......... *A61N 1/3962* (2013.01); *A61N 1/3981* (2013.01); *A61N 1/3987* (2013.01); *A61N 1/3782* (2013.01)

(56) References Cited

U.S. PATENT DOCUMENTS

| | | | |
|---|---|---|---|
| 5,824,018 A | 10/1998 | Dreher | |
| 6,778,860 B2 | 8/2004 | Ostroff | |
| 6,856,835 B2 | 2/2005 | Bardy | |
| 6,865,417 B2 | 3/2005 | Rissmann | |
| 6,952,608 B2 | 10/2005 | Ostroff | |
| 6,952,610 B2 | 10/2005 | Ostroff | |
| 6,954,670 B2 | 10/2005 | Ostroff | |
| 7,092,754 B2 | 8/2006 | Bardy | |
| 7,146,212 B2 | 12/2006 | Bardy | |
| 7,184,833 B2 | 2/2007 | Ganion | |
| 7,389,139 B2 | 6/2008 | Ostroff | |
| 7,392,081 B2 | 6/2008 | Wagner | |
| 7,471,983 B2 | 12/2008 | Voegele | |
| 7,502,645 B2 | 3/2009 | Ostroff | |
| 7,522,957 B2 | 4/2009 | Ostroff | |
| 7,751,885 B2 | 7/2010 | Bardy | |
| 7,761,150 B2 | 7/2010 | Ghanem | |
| 8,036,742 B2 | 10/2011 | Sullivan | |
| 8,155,740 B2 | 4/2012 | Wanasek | |
| 8,195,291 B2 | 6/2012 | Norton | |
| 8,359,094 B2 | 1/2013 | Bonner | |
| 8,412,320 B2 | 4/2013 | Ostroff | |
| 8,452,399 B2 | 5/2013 | Wanasek | |
| 8,758,365 B2 | 6/2014 | Bonner | |
| 8,914,105 B2 | 12/2014 | Wanasek | |
| 10,046,168 B2 * | 8/2018 | Nikolski | A61N 1/3987 |
| 2009/0210021 A1 | 8/2009 | Ostroff | |
| 2012/0197330 A1 | 8/2012 | Crutchfield | |
| 2014/0088659 A1 * | 3/2014 | Crutchfield | A61N 1/3987 607/7 |
| 2015/0300375 A1 | 10/2015 | Begon | |
| 2015/0306410 A1 | 10/2015 | Marshall | |
| 2016/0158567 A1 | 6/2016 | Marshall | |
| 2017/0157395 A1 | 6/2017 | Thompson-Nauman | |
| 2017/0157413 A1 | 6/2017 | Anderson | |

* cited by examiner

TACHYARRHYTHMIA INDUCTION BY AN EXTRA-CARDIOVASCULAR IMPLANTABLE CARDIOVERTER DEFIBRILLATOR

REFERENCE TO RELATED APPLICATION

This application is a continuation application of U.S. patent application Ser. No. 15/367,448, filed on Dec. 2, 2016, which claims the benefit of U.S. Provisional Application No. 62/262,500, filed on Dec. 3, 2015, the content of both of which are incorporated herein by reference in their entirety.

TECHNICAL FIELD

The disclosure relates generally to implantable medical devices and, in particular, to an implantable cardioverter defibrillator (ICD) and method for inducing tachyarrhythmia using extra-cardiovascular electrodes.

BACKGROUND

Medical devices, such as cardiac pacemakers and ICDs, provide therapeutic electrical stimulation to a heart of a patient via electrodes carried by one or more medical electrical leads and/or electrodes on a housing of the medical device. The electrical stimulation may include signals such as pulses or shocks for pacing, cardioversion or defibrillation. In some cases, a medical device may sense intrinsic depolarizations of the heart and control delivery of stimulation signals to the heart based on sensed cardiac electrical signals attendant to the depolarization of the myocardial tissue. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation.

In some cases, ventricular tachyarrhythmia is intentionally induced in a patient by delivering electrical stimulation to the patient's heart in a manner that is arrhythmogenic. Ventricular tachyarrhythmia may be induced in order to analyze the performance of an ICD in detecting the ventricular tachyarrhythmia and terminating it. A patient receiving an ICD to treat atrial or ventricular fibrillation or tachycardia may undergo defibrillation threshold testing in order to ensure reasonable certainty of successful defibrillation using shock pulse energies within the output capacity of the ICD. Some ICDs determine the defibrillation threshold by inducing fibrillation and subsequently delivering one or more defibrillation shocks to verify successful defibrillation at a delivered shock energy that is at least a safety margin below the maximum output of the ICD.

SUMMARY

In general, the disclosure is directed to techniques for inducing ventricular tachyarrhythmia by a cardiac defibrillation system, such as an extra-cardiovascular ICD system. An ICD operating according to the techniques disclosed herein delivers electrical stimulation pulses using extra-cardiovascular electrodes to induce a tachyarrhythmia. In some cases a high frequency burst of pulses is delivered to induce tachyarrhythmia. In other examples, a T-wave shock is delivered to induce tachyarrhythmia.

In one example, the disclosure provides an extra-cardiovascular ICD having a sensing module for acquiring a cardiac electrical signal; a high voltage therapy module comprising a high voltage charging circuit, a high voltage capacitor, and switching circuitry configured to couple the high voltage capacitor to a plurality of implantable extra-cardiovascular electrodes; and a control module. The control module is configured to control the high voltage therapy module to induce a tachyarrhythmia by controlling the high voltage therapy module to charge the high voltage capacitor to a first voltage amplitude, deliver a series of pulses having an inter-pulse interval between consecutive pulses to a patient's heart by enabling the switching circuitry to discharge the high voltage capacitor via an extra-cardiovascular electrode vector of the plurality of implantable extra-cardiovascular electrodes, and recharge the high voltage capacitor during the first inter-pulse interval between consecutive pulses of the first series of pulses. The control module is further configured to determine from the cardiac electrical signal if tachyarrhythmia is induced after the first series of pulses. In response to determining that tachyarrhythmia is induced, the control module controls the high voltage therapy module to charge the high voltage capacitor to a second voltage amplitude greater than the first voltage amplitude, the second voltage amplitude corresponding to a therapeutic shock energy and discharge the high voltage capacitor to deliver the therapeutic shock energy to the patient's heart.

In another example, the disclosure provides a method performed by an extra-cardiovascular ICD to induce a tachyarrhythmia. The method includes charging a high voltage capacitor of a high voltage therapy module by a high voltage charging circuit of the ICD to a first voltage amplitude, delivering a series of pulses having an inter-pulse interval between consecutive pulses to a patient's heart by enabling switching circuitry of the high voltage therapy module to discharge the high voltage capacitor via an extra-cardiovascular electrode vector of a plurality of implantable extra-cardiovascular electrodes, and recharging the high voltage capacitor during the inter-pulse interval between consecutive pulses of the series of pulses. The method further includes receiving a cardiac electrical signal by a sensing module of the ICD, determining from the cardiac electrical signal if tachyarrhythmia is induced after the first series of pulses. In response to determining that tachyarrhythmia is induced, the method includes charging the high voltage capacitor to a second voltage amplitude greater than the first voltage amplitude, the second voltage amplitude corresponding to a therapeutic shock energy, and discharging the high voltage capacitor to deliver the therapeutic shock energy to the patient's heart.

In another example, the disclosure provides a non-transitory, computer-readable storage medium comprising a set of instructions which, when executed by a control module of an extra-cardiovascular ICD, cause the ICD to charge a high voltage capacitor of a high voltage therapy module by a high voltage charging circuit of the ICD to a first voltage amplitude, deliver a series of pulses having an inter-pulse interval between consecutive pulses to a patient's heart by enabling switching circuitry of the high voltage therapy module to discharge the high voltage capacitor via an extra-cardiovascular electrode vector of a plurality of implantable extra-cardiovascular electrodes, and recharge the high voltage capacitor during the inter-pulse interval between consecutive pulses of the series of pulses. The ICD is further caused to receive a cardiac electrical signal by a sensing module of the ICD and determine from the cardiac electrical signal if tachyarrhythmia is induced after the series of pulses. In response to determining that tachyarrhythmia is induced, the ICD is further caused to charge the high voltage capacitor to a second voltage amplitude greater than the first voltage amplitude, the second voltage amplitude corresponding to a therapeutic shock energy, and discharge the high voltage capacitor to deliver the therapeutic shock energy to the patient's heart.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for delivering electrical stimulation pulses using implanted, extra-cardiovascular electrodes for inducing ventricular tachyarrhythmia in a patient. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but not in intimate contact with myocardial tissue. The techniques disclosed herein provide a method for inducing tachyarrhythmia using extra-cardiovascular electrodes without requiring transvenous leads or electrodes to be placed within the heart or vasculature of the patient.

Tachyarrhythmia induction may be performed in order to test the performance of the ICD upon implantation. Extra-cardiovascular ICD systems have been introduced for sensing cardiac signals for detecting abnormal heart rhythms and for delivering cardioversion/defibrillation (CV/DF) shocks for treating life-threatening ventricular tachyarrhythmias, such as ventricular fibrillation (VF) or fast ventricular tachycardia (VT). The techniques disclosed herein provide methods for inducing ventricular tachyarrhythmia without requiring the use of transvenous leads or intracardiac electrodes. By using these techniques, an extra-cardiovascular ICD system can be implanted and tested by inducing tachyarrhythmia without requiring the placement of additional leads or electrodes.

Figure 1A:
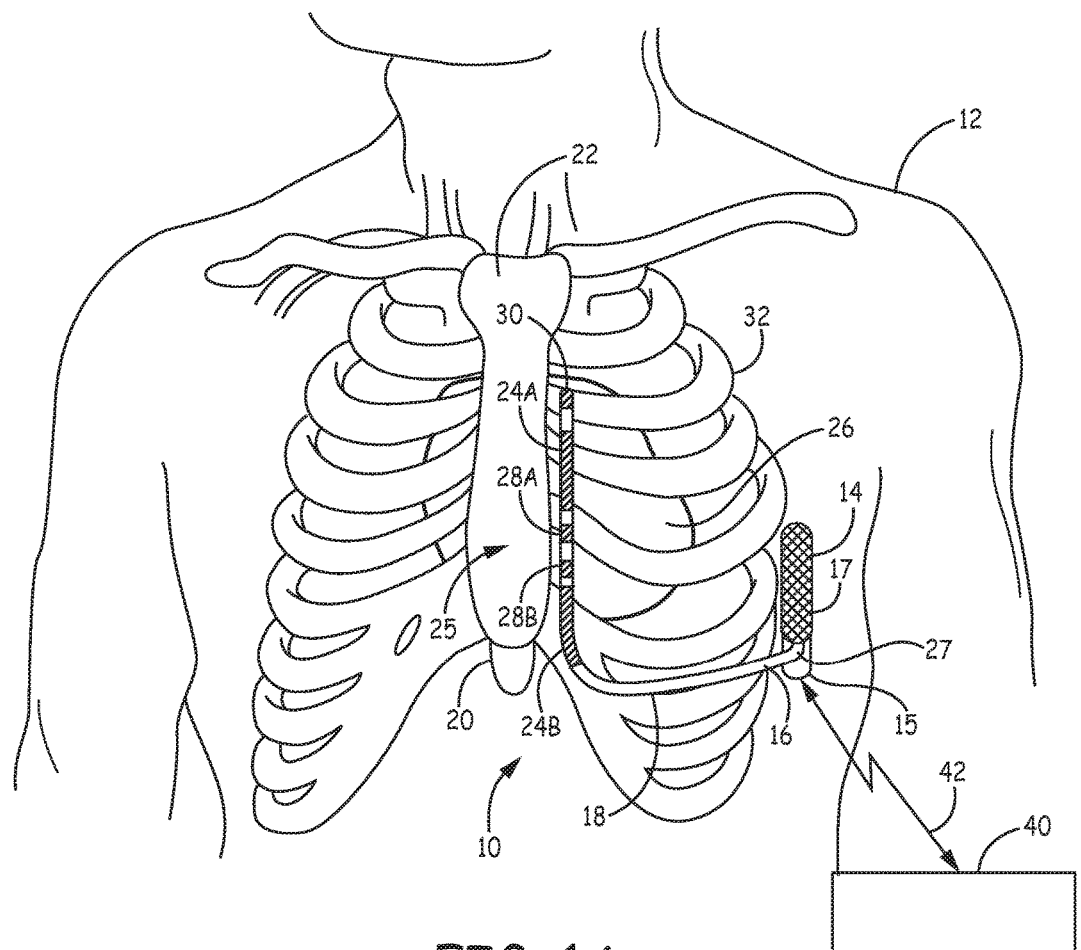
FIGS. 1A and 1B are conceptual diagrams of an extra-cardiovascular ICD system according to one example.
Figure 1B:
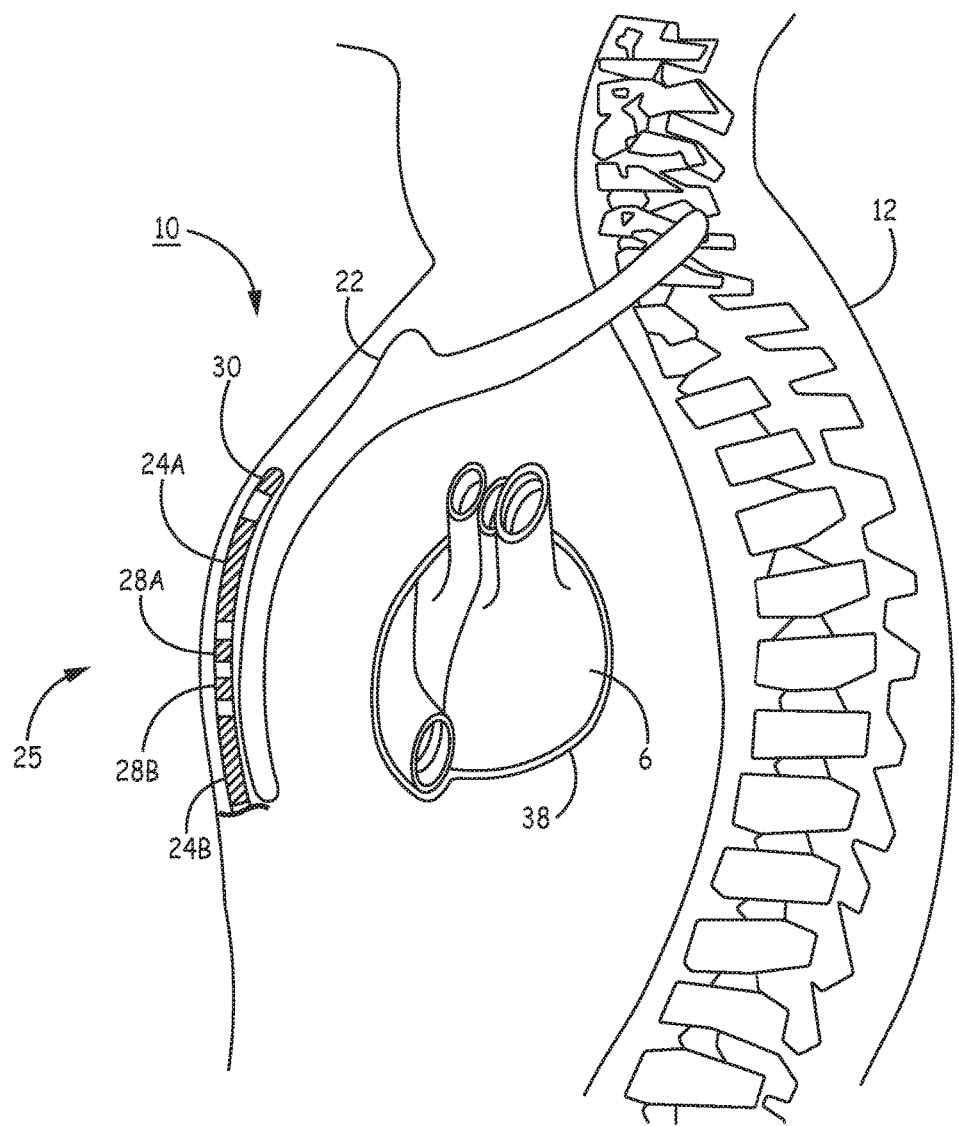

FIGS. 1A and 1B are conceptual diagrams of an extra-cardiovascular ICD system 10. FIG. 1A is a frontal view of ICD system 10 implanted within patient 12. FIG. 1B is a side view of ICD system 10 implanted within patient 12. ICD system 10 includes an ICD 14 connected to an extra-cardiovascular electrical stimulation lead 16. FIGS. 1A and 1B are described in the context of an ICD system 10 capable of providing defibrillation and/or cardioversion shocks and, in some instances, cardiac pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a "can" electrode). In other instances, the housing of ICD 14 may include a plurality of electrodes on an outer portion of the housing. The outer portion(s) of the housing 15 functioning as an electrode(s) may be coated with a material, such as titanium nitride. ICD 14 includes a connector assembly 17 (also referred to as a connector block or header) that includes electrical feedthroughs crossing housing 15 to provide electrical connections between conductors extending within an elongated lead body 18 and electronic components included within the housing 15 of ICD 14. As will be described in further detail herein, housing 15 may house one or more processors, memories, transceivers, sensors, electrical sensing circuitry, therapy circuitry, power sources and other appropriate components.

Elongated lead body 18 extends from a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24A and 24B, collectively 24, and pace/sense electrodes 28A, 28B, and 30. In some cases, defibrillation electrodes 24A and 24B may together form a defibrillation electrode in that they are configured to be activated concurrently. Alternatively, defibrillation electrodes 24A and 24B may form separate defibrillation electrodes in which case each of the electrodes 24A and 24B may be activated independently. In some instances, ICD 14 may include switching mechanisms to allow defibrillation electrodes 24A and 24B coupled to electrically isolated conductors to be utilized as a single defibrillation electrode (e.g., activated concurrently to form a common cathode or anode) or as separate defibrillation electrodes, (e.g., activated individually).

Electrodes 24A and 24B are referred to as defibrillation electrodes because they are utilized, individually or collectively, for delivering high voltage stimulation therapy (e.g., cardioversion or defibrillation shocks). Electrodes 24A and 24B may be elongated coil electrodes and generally have a relatively high surface area for delivering high voltage electrical stimulation pulses compared to low voltage pacing and sensing electrodes 28A, 28B and 30. However, electrodes 24A and 24B may also be utilized to provide pacing functionality, sensing functionality or both pacing and sensing functionality in addition to or instead of high voltage stimulation therapy. In this sense, the use of the term "defibrillation electrode" should not be considered as limiting the electrodes 24A and 24B for use in only high voltage therapy applications. Furthermore, electrical stimulation pulses delivered using electrodes 24A and 24B are not limited to therapeutic pulses used to treat an abnormal rhythm. In particular, as described herein, electrodes 24A and 24B may be used to deliver electrical stimulation pulses for inducing tachyarrhythmia during testing of ICD system 10.

Lead 16 extends subcutaneously or submuscularly over the ribcage 32 from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14 or other factors.

Electrical conductors (not illustrated) extend through one or more lumens of the elongated lead body 18 of lead 16, from the lead connector at the proximal lead end 27 to defibrillation electrodes 24A and 24B and pace/sense electrodes 28A, 28B, and 30 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions or to any particular lead body design.

The one or more elongated electrical conductors contained within the lead body 18 are electrically coupled with respective defibrillation electrodes 24A and 24B and pace/sense electrodes 28A, 28B, and 30. In one example, each of electrodes 28A, 28B, and 30 is electrically coupled to a respective insulated conductor within the lead body 18. ICD 14 may include a switch module that may enable electrically isolated conductors of both defibrillation electrodes 24A and 24B to be jumpered, tied or otherwise electrically connected such that defibrillation electrodes 24A and 24B may be electrically coupled together to be simultaneously used as a common anode or cathode of an electrode vector for delivery of electrical stimulation pulses to patient 12 and/or for sensing the electrical signals of the heart 26 of the patient 12.

The respective conductors electrically couple the electrodes 24A, 24B, 28A, 28B and 30 to circuitry, such as a therapy module or a sensing module, of ICD 14 via connections in the connector assembly 17, including associated electrical feedthroughs crossing housing 15. The electrical conductors transmit therapy from a therapy module within ICD 14 to one or more of defibrillation electrodes 24A and 24B and/or pace/sense electrodes 28A, 28B, and 30 and transmit sensed electrical signals from one or more of defibrillation electrodes 24A and 24B and/or pace/sense electrodes 28A, 28B, and 30 to the sensing module within ICD 14.

Electrodes 28A, 28B and 30 are referred to as pace/sense electrodes because they are generally configured for use in low voltage applications, e.g., used as either a cathode or anode for delivery of pacing pulses and/or sensing of cardiac electrical signals. In some instances, electrodes 28A, 28B, and 30 may provide only pacing functionality, only sensing functionality or both. Furthermore, electrodes 28A, 28B and/or 30 may be used in combination with each other, with housing 15 and/or with one or both of electrodes 24A and 24B for delivering electrical pulses for inducing tachyarrhythmia.

In the example of FIGS. 1A and 1B, electrodes 28A and 28B are illustrated as ring electrodes and electrode 30 is illustrated as a hemispherical tip electrode. However, electrodes 28A, 28B, and 30 may comprise any of a number of different types of electrodes, including ring electrodes, short coil electrodes, paddle electrodes, hemispherical electrodes, directional electrodes, segmented electrodes, or the like, and may be positioned at any position along the distal portion 25 of lead 16. Further, electrodes 28A, 28B, and 30 may be of similar type, shape, size and material or may differ from each other.

In the example illustrated in FIGS. 1A and 1B, electrodes 28A and 28B are located between defibrillation electrodes 24A and 24B and electrode 30 is located distal to defibrillation electrode 24A. FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes. The pace/sense electrodes 28A, 28B, and 30 may be located elsewhere along the length of lead 16, e.g., distal to defibrillation electrode 24A, proximal to defibrillation electrode 24B, and/or between electrodes 24A and 24B. For example, lead 16 may include a single pace/sense electrode 28 between defibrillation electrodes 24A and 24B and no pace/sense electrode distal to defibrillation electrode 24A or proximal to defibrillation electrode 24B. In still other instances, there may be no discrete pace/sense electrodes, in which case the defibrillation electrodes 24A and 24B may be utilized for sensing, delivering pulses for inducing tachyarrhythmia, delivering pacing pulses such as post-shock pacing pulses, as well as delivering high voltage cardioversion or defibrillation shock pulses.

Various example configurations of electrodes and dimensions that may be implemented in conjunction with the induction techniques disclosed herein are described in pending U.S. Pat. Publication No. 2015/0306375 (Marshall, et al.) and U.S. Pat. Publication No. 2015/0306410 (Marshall, et al.), both of which are incorporated herein by reference in their entirety. In still other examples, ICD system 10 of FIGS. 1A and 1B may include a second extra-cardiovascular electrical stimulation and sensing lead similar to lead 16. The second lead may, for example, extend laterally to the posterior of patient 12 and include one or more electrodes that form an electrode vector with one or more of electrodes 24A, 24B, 28A, 28B, and/or 30 of lead 16 for providing pacing in accordance with the techniques disclosed herein.

In some instances, electrodes 24A, 24B, 28A, 28B, and/or 30 of lead 16 may be shaped, oriented, designed or otherwise configured to reduce extra-cardiac stimulation. For example, electrodes 24A and 24B and/or electrodes 28A, 28B, and/or 30 of lead 16 may be shaped, oriented, designed, partially insulated or otherwise configured to focus, direct or point electrodes 24A and 24B and/or electrodes 28A, 28B, and/or 30 toward heart 26. In this manner, electrical stimulation pulses delivered via lead 16 are directed toward heart 26 and not outward toward skeletal muscle. For example, electrodes 24A and 24B and/or electrodes 28A, 28B, and/or 30 of lead 16 may be partially coated or masked with a polymer (e.g., polyurethane) or another coating material (e.g., tantalum pentoxide) on one side or in different regions so as to direct the electrical energy toward heart 26 and not outward toward skeletal muscle. In the case of a ring electrode, for example, the ring electrode may be partially coated with the polymer or other material to form a half-ring electrode, quarter-ring electrode, or other partial-ring electrode. When ICD 14 delivers electrical stimulation via electrodes 24A, 24B, 28A, 28B and/or 30 for inducing a tachyarrhythmia, recruitment of surrounding skeletal muscle, which can cause pain or discomfort to the patient, may be reduced by shaping, orienting, or partially insulating electrodes 24A, 24B, 28A, 28B and/or 30 to focus or direct electrical energy toward heart 26.

ICD 14 may obtain electrical signals corresponding to electrical activity of heart 26 via a combination of sensing electrode vectors that include combinations of electrodes 28A, 28B, and 30 and the housing 15 of ICD 14. In some instances, ICD 14 may even obtain sensed electrical signals using a sensing electrode vector that includes one or both defibrillation electrodes 24A or 24B such as between each other or in combination with one or more of electrodes 28A, 28B, and 30, and/or the housing 15.

ICD 14 analyzes the sensed electrical signals obtained from one or more of the sensing vectors to monitor for tachyarrhythmia, such VT or VF. ICD 14 may analyze the heart rate and/or morphology of the sensed electrical signals to monitor for tachyarrhythmia, including induced tachyarrhythmia, in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver one or more cardioversion or defibrillation shocks via one or both of defibrillation electrodes 24A and 24B and/or housing 15. ICD 14 may deliver the cardioversion or defibrillation shocks using electrodes 24A and 24B individually or together as a cathode (or anode) and with the housing 15 as an anode (or cathode). ICD 14 may generate and deliver electrical stimulation other than cardioversion or defibrillation shocks, including anti-tachycardia pacing (ATP), post-shock pacing, pulse burst delivery for tachyarrhythmia induction, and/or entrainment pacing pulses before a T-shock, also referred to herein as a "T-wave shock," for tachyarrhythmia induction using a therapy vector formed from one or more of a variety of electrode vectors that include one or more of the electrodes 24A and 24B and/or electrodes 28A and/or 28B and/or 30, and/or the housing 15 of ICD 14. As described below, ICD 14 is configured to induce tachyarrhythmia by delivering a series of pulses to the patient's heart 26 via extra-cardiovascular electrodes, e.g., at least one electrode carried by lead 16. The series of pulses may include a burst of pulses to induce ventricular tachyarrhythmia using extra-cardiovascular electrodes 24A, 24B 28A, 28B and/or 30. A series of tachyarrhythmia induction pulses delivered as a burst of pulses is delivered at a frequency that is greater than a physiological heart rate, for example greater than 10 Hz or between 20 Hz and 50 Hz inclusive in some examples. In other examples, ICD 14 may be configured to deliver a series of pulses for inducing tachyarrhythmia by delivering one or more entrainment pacing pulses followed by a T-shock synchronized to a T-wave by delivering the T-shock at an R-T time interval following the last one of the entrainment pulses. The entrainment pulses and the T-shock may all be delivered using extra-cardiovascular electrodes 24A, 24B 28A, 28B and/or 30. The entrainment pulses may be delivered at an interpulse interval that does correspond to a physiological heart rate and is shorter than an intrinsic heart rate interval to overdrive pace the heart and thereby control the heart rate and enable proper synchronization of the T-shock with the T-wave attendant to the repolarization of the myocardium.

ICD 14 generates and delivers electrical stimulation therapy in response to detecting a tachyarrhythmia (e.g., VT or VF), induced or a spontaneous, intrinsic tachyarrhythmia. ICD 14 may deliver one or more cardioversion or defibrillation shocks via one or both of defibrillation electrodes 24A and 24B and/or housing 15 in response to detecting VT or VF. ICD 14 may deliver the cardioversion or defibrillation shocks using electrodes 24A and 24B individually or together as a cathode (or anode) and with the housing 15 as an anode (or cathode).

ICD 14 may generate and deliver therapeutic electrical stimulation pulses other than cardioversion or defibrillation shocks in response to detecting cardiac arrhythmias, including bradycardia pacing pulses, anti-tachycardia pacing (ATP) pulses, and post-shock pacing or asystole pacing pulses using a therapy vector formed from one or more of any of a variety of electrode vectors that include one or more of the electrodes 24A, 24B, 28A, 28B and/or 30, and/or the housing 15 of ICD 14. ICD 14 may be configured to select a pacing output configuration using either a low voltage therapy module or a high voltage therapy module and a pacing electrode vector selected from among electrodes 24A, 24B, 28A, 28B, 30 and housing 15 for delivering a pacing therapy (e.g., ATP, asystole pacing post-shock or during atrioventricular conduction block, or bradycardia pacing) or for delivering a tachyarrhythmia induction sequence that includes entrainment pacing pulses prior to a T-shock or high frequency burst pulses (e.g., 50 Hz burst pulses). Selection of a pacing output configuration may be performed according to the techniques disclosed in U.S. Patent Application No. 62/262,499 and corresponding U.S. patent application Ser. No. 15/367,516 (Anderson, et al., filed on the same day herewith), incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this example, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum 22 or ribcage 32 in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac rhythm detection parameters and therapy control parameters used by ICD 14. Control parameters used to generate and deliver tachyarrhythmia induction pulses may also be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
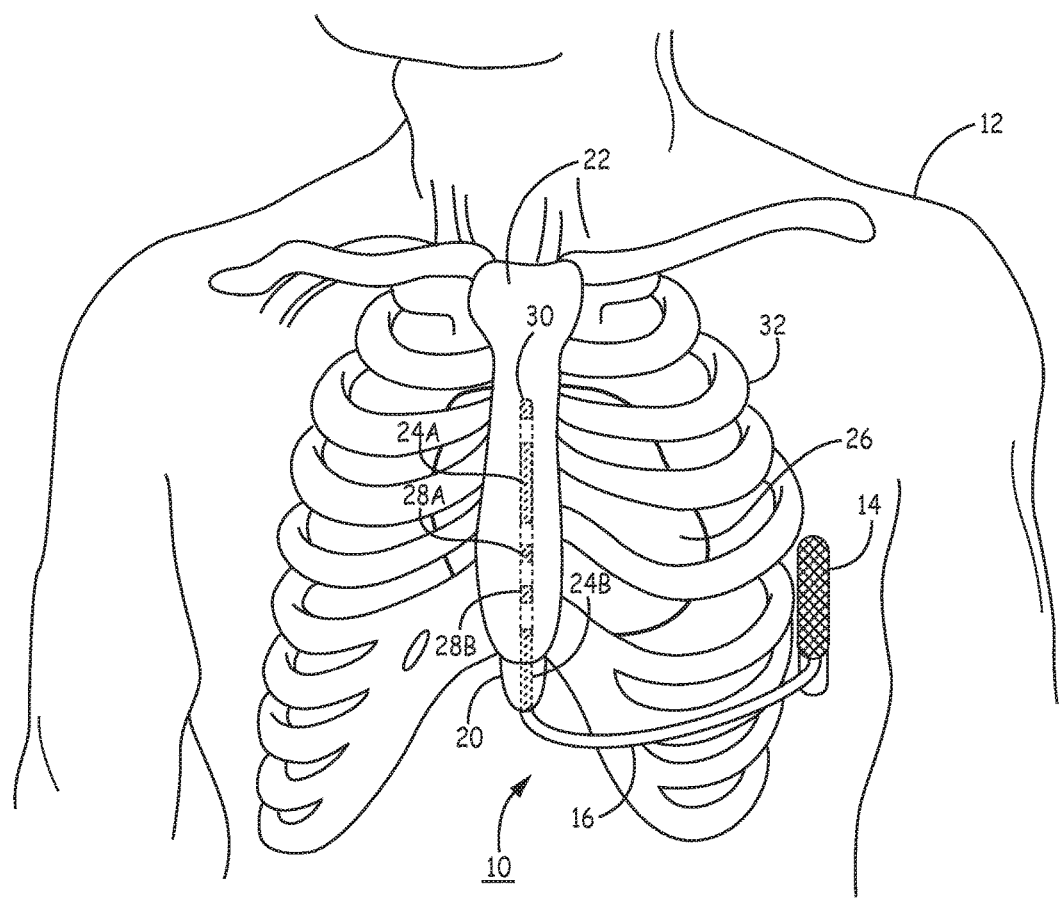
FIGS. 2A-2C are conceptual diagrams of a patient implanted with the extra-cardiovascular ICD system of FIGS. 1A and 1B in a different implant configuration.
Figure 2B:
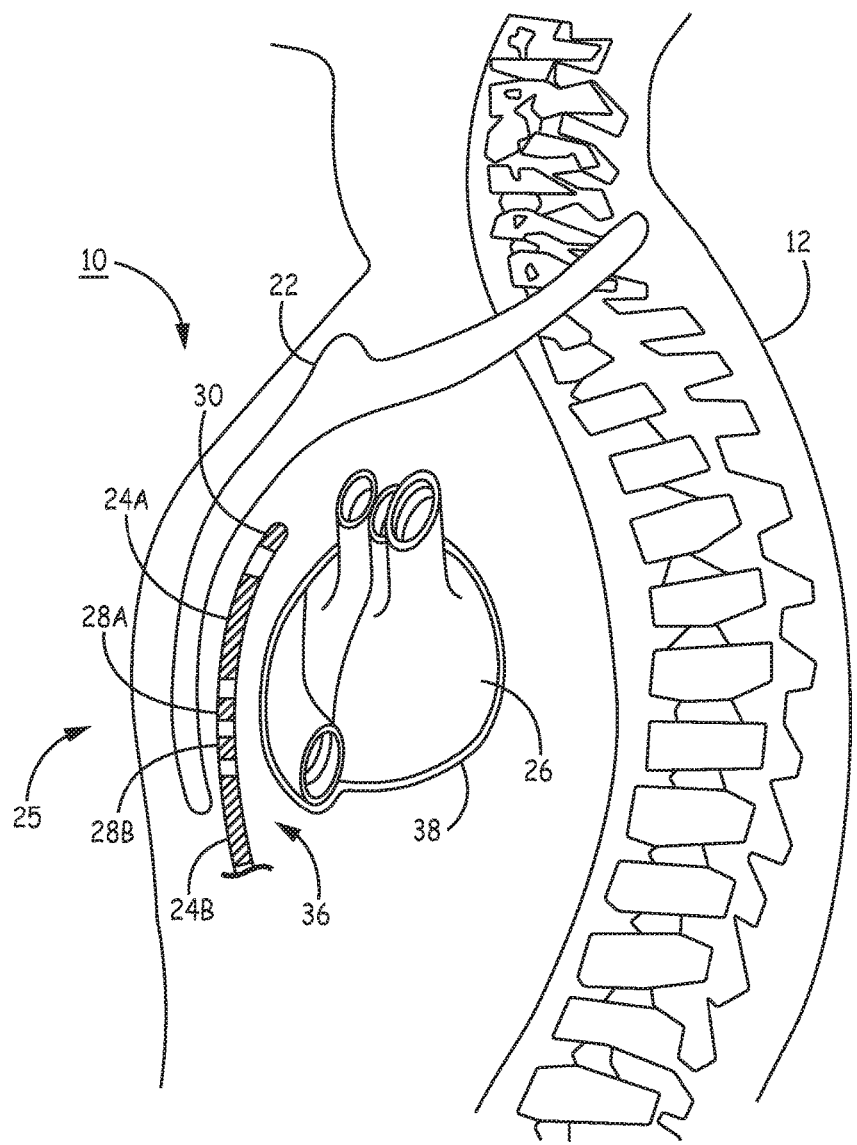
Figure 2C:
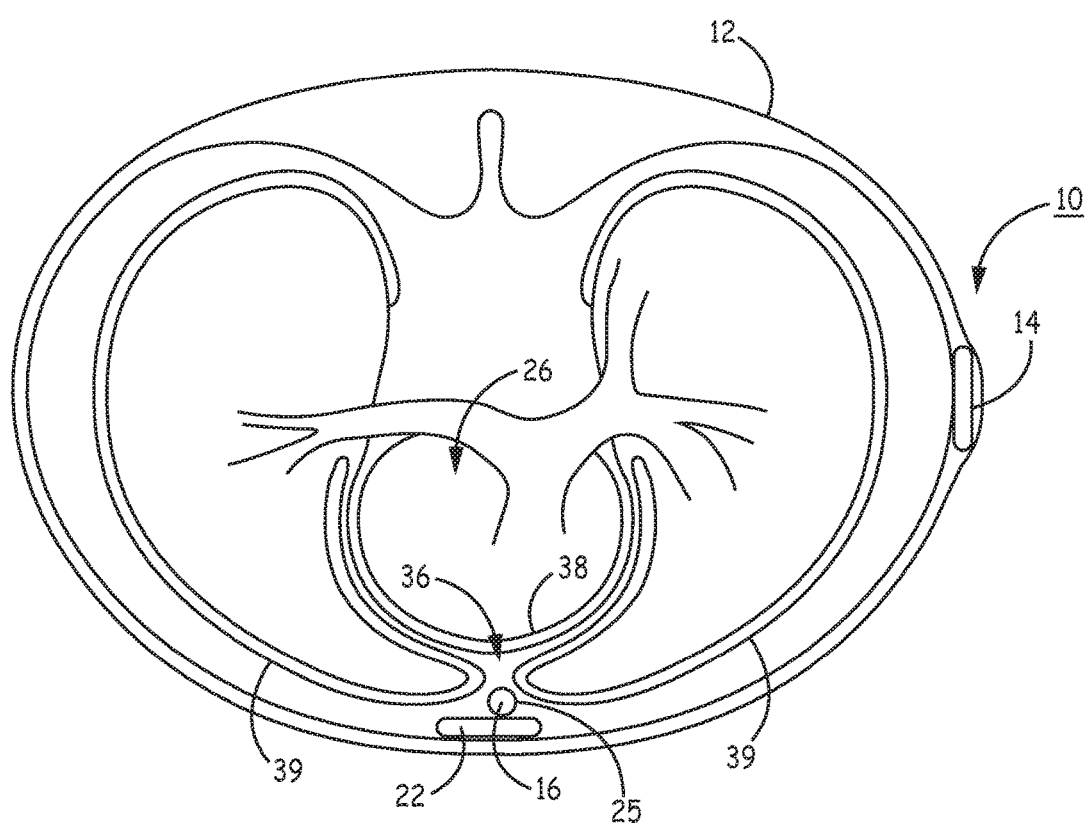

FIGS. 2A-2C are conceptual diagrams of patient 12 implanted with ICD system 10 in a different implant configuration than the arrangement shown in FIGS. 1A-1B. FIG. 2A is a frontal view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, the thymus gland, substernal musculature, and small side branches of the internal thoracic artery and the internal thoracic vein. In one example, the distal portion of lead 16 extends along the posterior side of sternum 22 substantially within the loose connective tissue and/or substernal musculature of anterior mediastinum 36. Lead 16 may be at least partially implanted in other extra-cardiovascular, intrathoracic locations, e.g., along ribcage 32 or along or adjacent to the perimeter of the pericardium or within the pleural cavity.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. Other implant locations and lead and electrode arrangements that may be used in conjunction with the tachyarrhythmia induction techniques described herein are generally disclosed in the above-incorporated patent references. Although example extra-cardiovascular locations are described above with respect to FIGS. 1A, 1B and 2A-2C, the techniques of this disclosure for inducing tachyarrhythmias may be utilized in other implementations of ICD, lead and electrode locations.

Figure 3:
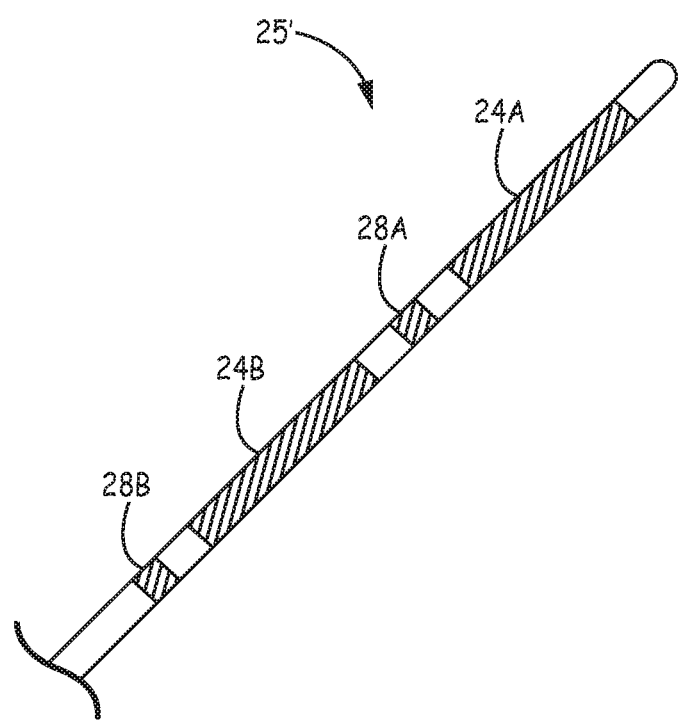
FIG. 3 is a conceptual diagram illustrating a distal portion of the extra-cardiovascular lead of FIG. 1A having an alternative electrode arrangement.

FIG. 3 is a conceptual diagram illustrating a distal portion 25' of another example of implantable electrical lead 16 having an alternative electrode arrangement. In this example, distal portion 25' includes two pace/sense electrodes 28A and 28B and two defibrillation electrodes 24A and 24B and respective conductors (not shown) to provide the electrical stimulation and sensing functionality as described above in conjunction with FIGS. 1A, 1B and FIGS. 2A-2C. In this example, however, electrode 28B is proximal to proximal defibrillation electrode 24B, and electrode 28A is distal to proximal defibrillation electrode 24B such that electrodes 28A and 28B are separated by defibrillation electrode 24B. In a further example, in addition to electrodes 28A and 28B, lead 16 may include a third pace/sense electrode located distal to defibrillation electrode 24A.

The spacing and location of pace/sense electrodes 28A and 28B may be selected to provide pacing and sensing vectors that enable efficient pacing and sensing of heart 26. The lengths and spacing of electrodes 24A, 24B, 28A and 28B may correspond to any of the examples provided in the above-incorporated references. For example, the distal portion 25' of lead 16 from the distal end to the proximal side of the most proximal electrode (e.g., electrode 28B in the example of FIG. 3) may be less than or equal to 15 cm and may be less than or equal to 13 cm and may even be less than or equal to 10 cm. It is contemplated that one or more pace/sense electrodes may be distal to distal defibrillation electrode 24A, one or more pace/sense electrodes may be between defibrillation electrodes 24A and 24B, and/or one or more pace/sense electrodes may be proximal to proximal defibrillation electrode 24B. Having multiple electrodes at different locations along lead body 18 enables selection of a variety of inter-electrode spacings, which allows a pacing electrode pair (or combination) to be selected having an inter-electrode spacing that results in the greatest pacing efficiency.

ICD 14 may deliver electrical stimulation and/or sense electrical signals using any electrode vector that includes defibrillation electrodes 24A and 24B (individually or collectively), and/or electrodes 28A and/or 28B, and/or the housing 15 of ICD 14. For example, ICD 14 may deliver electrical pulses using a low voltage therapy module via an electrode vector in which one of electrodes 28A or 28B is selected as a cathode and the other of electrodes 28A and 28B is selected as the anode. Other examples of low-voltage therapy delivery electrode vectors may include one of electrodes 28A or 28B or both in combination selected as a cathode (or anode) with one of defibrillation electrodes 24A, 24B or housing 15 selected as an anode (or cathode). ICD 14 may deliver electrical pulses using a high voltage therapy module using an electrode vector that uses one or both of defibrillation electrodes 24A and 24B as a cathode (or anode) and the housing 15 of ICD 14 as an anode (or cathode). In still other examples, stimulation pulses may be delivered "coil-to-coil" between electrodes 24A and 24B or "ring-to-coil" between one of electrodes 28A or 28B and one of electrodes 24A or 24B.

Figure 4:
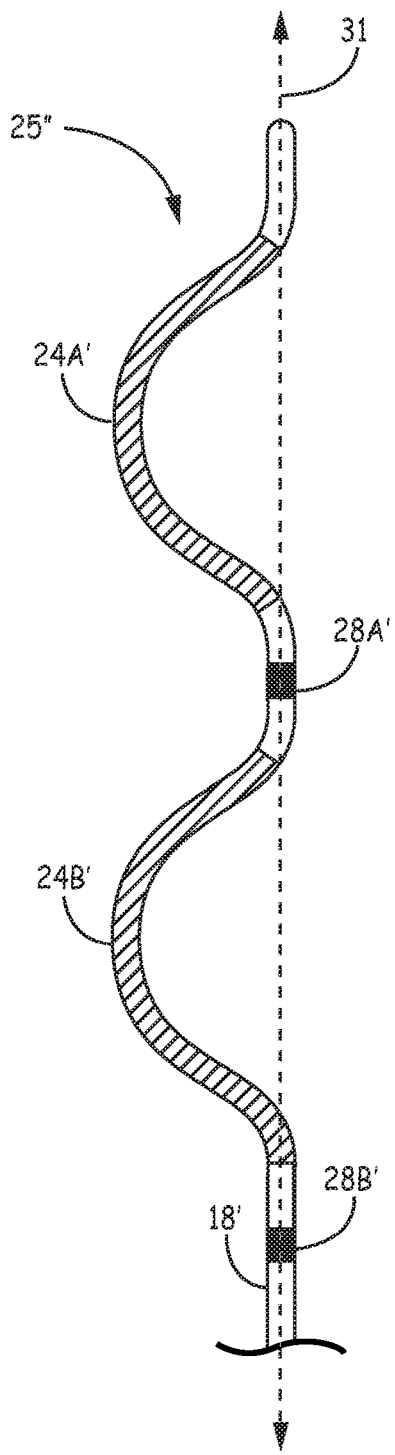
FIG. 4 is a conceptual diagram illustrating a distal portion of the extra-cardiovascular lead of FIG. 1A according to yet another example.

FIG. 4 is a conceptual diagram illustrating a distal portion 25" of another example of extra-cardiovascular lead 16 having an electrode arrangement similar to that of FIG. 3 but with a non-linear or curving distal portion 25" of lead body 18'. Lead body 18' may be pre-formed to have a normally curving, bending, serpentine, undulating, or zig-zagging shape along distal portion 25". In this example, defibrillation electrodes 24A' and 24B' are carried along curving portions of the lead body 18'. Pace/sense electrode 28A' is carried between defibrillation electrodes 24A' and 24B'. Pace/sense electrode 28B' is carried proximal to the proximal defibrillation electrode 24B'.

In one example, lead body 18' may be formed having a curving distal portion 25" that includes two "C" shaped curves, which together may generally resemble the Greek letter epsilon, "ε." Defibrillation electrodes 24A' and 24B' are each carried by the two respective C-shaped portions of the lead body distal portion 25" and extend or curve in the same direction. In the example shown, pace/sense electrode 28A' is proximal to the C-shaped portion carrying electrode 24A', and pace/sense electrode 28B' is proximal to the C-shaped portion carrying electrode 24B'.

Pace/sense electrodes 24A' and 24B' may be approximately aligned with a central axis 31 of the straight, proximal portion of lead body 18' such that mid-points of defibrillation electrodes 24A' and 24B' are laterally offset from electrodes 28A' and 28B'. Defibrillation electrodes 24A' and 24B' are located along respective C-shaped portions of the lead body distal portion 25" that extend laterally in the same direction away from central axis 31 and electrodes 28A' and 28B'. Other examples of extra-cardiovascular leads including one or more defibrillation electrodes and one or more pacing and sensing electrodes carried by a curving, serpentine, undulating or zig-zagging distal portion of the lead body that may be implemented with the tachyarrhythmia induction techniques described herein are generally disclosed in pending U.S. Pat. Publication No. 2016/0158567 (Marshall, et al.), incorporated herein by reference in its entirety.

Figure 5:
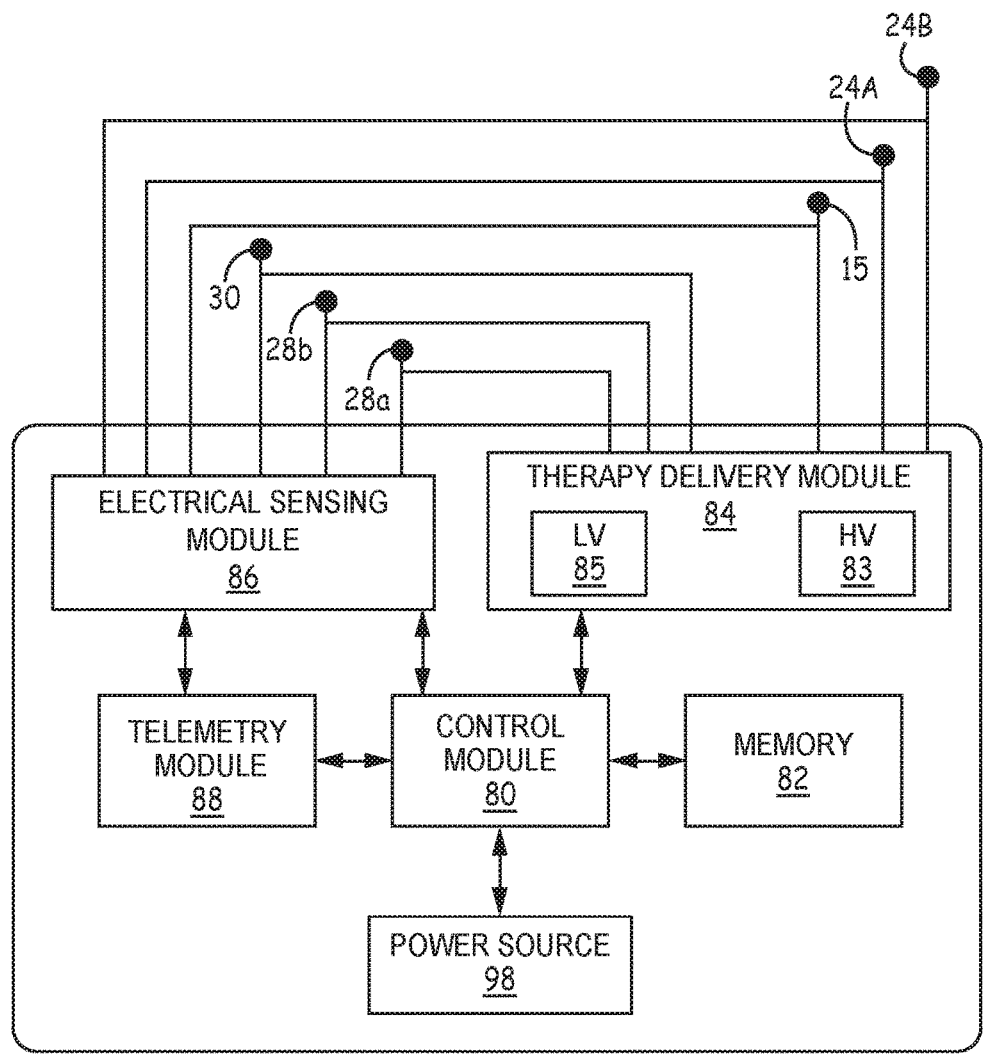
FIG. 5 is a schematic diagram of the ICD of the system of FIGS. 1A-2C according to one example.

FIG. 5 is a schematic diagram of ICD 14 according to one example. The electronic circuitry enclosed within housing 15 (shown schematically as a can electrode in FIG. 5) includes software, firmware and hardware that cooperatively monitor one or more cardiac electrical signals, determine when an electrical stimulation therapy is necessary, and deliver prescribed electrical stimulation therapies as needed. For example, the software, firmware and hardware is configured to determine when a CV/DF shock or cardiac pacing is necessary, and deliver prescribed CV/DF shock therapies or pacing therapies. ICD 14 may be coupled to an extra-cardiovascular lead, such as lead 16 shown in any of the examples of FIGS. 1A-4, carrying extra-cardiovascular electrodes 24A, 24B, 28A, 28B and 30 (when present), for delivering pacing therapies, CV/DF shock therapies and sensing cardiac electrical signals. As described below, ICD 14 is configured to induce tachyarrhythmia by delivering electrical stimulation induction pulses using any of the extra-cardiovascular electrodes 24A, 24B, 28A, 28B and 30.

ICD 14 includes a control module 80, memory 82, therapy delivery module 84, electrical sensing module 86, and telemetry module 88. A power source 98 provides power to the circuitry of ICD 14, including each of the modules 80, 82, 84, 86, and 88 as needed. Power source 98 may include one or more energy storage devices, such as one or more rechargeable or non-rechargeable batteries. The connections between power source 98 and each of the other modules 80, 82, 84, 86 and 88 are to be understood from the general block diagram of FIG. 5, but are not shown for the sake of clarity. For example, power source 98 is coupled to low voltage (LV) and high voltage (HV) charging circuits included in therapy delivery module 84 for charging LV and HV capacitors, respectively, or other LV and HV energy storage devices included in therapy delivery module 84 for generating therapeutic electrical stimulation pulses and for generating tachyarrhythmia induction pulses.

The functional blocks shown in FIG. 5 represent functionality included in ICD 14 and may include any discrete and/or integrated electronic circuit components that implement analog and/or digital circuits capable of producing the functions attributed to ICD 14 herein. As used herein, the term "module" refers to an application specific integrated circuit (ASIC), an electronic circuit, a processor (shared, dedicated, or group) and memory that execute one or more software or firmware programs, a combinational logic circuit, state machine, capacitors, switching circuitry, or other suitable components that provide the described functionality. The particular form of software, hardware and/or firmware employed to implement the functionality disclosed herein will be determined primarily by the particular system architecture employed in the device and by the particular detection and therapy delivery methodologies employed by the ICD 14. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14 or those ICD modules. The non-transitory, computer-readable media storing the instructions may include any of the media listed above.

Depiction of different modules in FIG. 5 is intended to highlight different functional aspects of ICD 14 and does not necessarily imply that such modules must be realized by separate hardware or software components. Rather, functionality associated with one or more modules may be performed by separate hardware, firmware or software components, or integrated within common hardware, firmware or software components. For example, tachyarrhythmia induction operations performed by control module 80 and therapy delivery module 84 may include operations implemented in a processor executing instructions stored in memory 82.

Control module 80 communicates with therapy delivery module 84 and electrical sensing module 86 for sensing cardiac electrical activity, detecting cardiac rhythms, and controlling delivery of cardiac electrical stimulation therapies in response to sensed cardiac signals. Therapy delivery module 84 and electrical sensing module 86 are electrically coupled to electrodes 24A, 24B, 28A, 28B, and 30 carried by lead 16 and the housing 15, which may function as a common or ground electrode or as an active can electrode for delivering CV/DF shock pulses or T-shock pulses used to induce tachyarrhythmia.

Electrical sensing module 86 may be selectively coupled to electrodes 28A, 28B, 30 and housing 15 in order to monitor electrical activity of the patient's heart. Electrical sensing module 86 may additionally be selectively coupled to electrodes 24A and/or 24B. Sensing module 86 is enabled to selectively monitor one or more sensing electrode vectors selected from the available electrodes 24A, 24B, 28A, 28B, 30 and 15. For example, sensing module 86 may include switching circuitry for selecting which of electrodes 24A, 24B, 28A, 28B, 30 and 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes. The cardiac event detection circuitry within electrical sensing module 86 may include one or more sense amplifiers, filters, rectifiers, threshold detectors, comparators, analog-to-digital converters (ADCs), or other analog or digital components.

In some examples, electrical sensing module 86 includes multiple sensing channels for acquiring cardiac electrical signals from multiple sensing vectors selected from electrodes 24A, 24B, 28A, 28B, 30 and 15. Each sensing channel may be configured to amplify, filter, digitize and rectify the cardiac electrical signal received from selected electrodes coupled to the respective sensing channel to improve the signal quality for sensing cardiac events, e.g., P-waves and R-waves. Each sensing channel includes cardiac event detection circuitry for sensing cardiac events from the received cardiac electrical signal developed across the selected sensing electrode vector(s). The sensed cardiac events, e.g., P-waves and R-waves, may be used for detecting cardiac rhythms and determining a need for therapy. For example, sensed R-waves may be used for detecting induced ventricular tachyarrhythmia and verifying that a delivered shock therapy has successfully terminated the induced tachyarrhythmia.

Therapy delivery module 84 includes an LV therapy module 85 for delivering low voltage pacing pulses using an extra-cardiovascular pacing electrode vector selected from electrodes 24A, 24B, 28A, 28B, 30 and 15. LV therapy module 85 may be configured to deliver low voltage pacing pulses, e.g., 8 V or less in some examples or 20 V or less in other examples. One or more capacitors included in the LV therapy module 85 are charged to a voltage according to a programmed pacing pulse amplitude by a LV charging circuit, which may include a state machine for charging capacitors to a multiple of the battery voltage included in power source 98. At an appropriate time, the LV therapy module 85 couples the capacitor(s) to a pacing electrode vector to deliver a pacing pulse to the heart 26. In some examples, ICD 14 does not include a LV therapy module 85 and all electrical stimulation pulses delivered by ICD 14 are produced by high voltage (HV) therapy module 83. When included, the LV therapy module includes holding capacitors that are charged for delivering LV electrical stimulation pulses and have a capacitance that is less than the capacitance of holding capacitors included in the HV therapy module 83. For example, LV therapy module holding capacitors charged for delivering LV electrical stimulation pulses may have a capacitance that is up to 20 microfarads.

HV therapy module 83 includes one or more high voltage capacitors, having a relatively high capacitance, e.g., 100 microfarads or more, which is greater than the capacitance of the LV therapy module capacitors. When a shockable rhythm is detected, the HV capacitor(s) is(are) charged to a voltage level by a HV charging circuit according to a programmed shock energy. The HV charging circuit may include a transformer and be a processor-controlled charging circuit that is controlled by control module 80. Control module 80 applies a signal to trigger discharge of the HV capacitor(s) upon detecting a feedback signal from therapy delivery module 84 indicating that the HV capacitors have reached the voltage required to deliver a programmed shock energy. In this way, control module 80 controls operation of the high voltage therapy module 83 to deliver CV/DF shocks using defibrillation electrodes 24A, 24B and/or housing 15.

HV therapy module 83 may be used to deliver a burst of pulses for inducing ventricular tachyarrhythmia during testing of ICD system 10. The burst of pulses and a subsequent CV/DF shock for terminating an induced tachyarrhythmia may be delivered via the same electrode vector, e.g., between electrodes 24A and 24B or between one of electrodes 24A or 24B and housing 15. To deliver the burst of pulses by HV therapy module 83, the HV capacitor is charged to a programmed voltage that is below that used to deliver a CV/DF shock. For example, the HV capacitor may be charged to 40 V or less, 30 V or less, or even 20 V or less for delivering tachyarrhythmia induction pulses in some examples. In most instances, the HV circuitry is generally designed for delivery of the high-voltage CV/DF shocks which are typically associated with voltages that are much higher than the 40 V, 30V, or 20V. For example, the voltages associated with CV/DF shocks may be at least ten times greater than those voltages. The HV circuitry of therapy delivery module 84 may only be capable of producing reduced level voltages to a certain minimum level. The minimum level may be 10V in one example. In other examples the minimum voltage level may be 15V or even 20V depending on the design.

For the sake of comparison, the HV capacitor(s) of the HV therapy module 83 may be charged to an effective voltage greater than 100 V for delivering a cardioversion/defibrillation shock. For example, two or three HV capacitors may be provided in series having an effective capacitance of 148 microfarads in HV therapy module 83. These series capacitors may be charged to develop 750 to 800 V for the series combination in order to deliver cardioversion/defibrillation shocks having a pulse energy of 5 Joules or more, and more typically 20 Joules or more. The pulse burst or entrainment pulses delivered by the HV therapy module 83 for inducing a tachyarrhythmia may have a pulse energy in the milliJoule range or at least tenths of milliJoules. For instance, an electrical stimulation pulse generated by HV therapy module 83 as part of a tachyarrhythmia induction sequence may be 10 V in amplitude with a 10 ms pulse width and in the range of 1 to 2.5 milliJoules when the electrode vector impedance is in the range of 400 to 1000 ohms.

When a tachyarrhythmia induction burst of pulses is delivered, control module 80 performs tachyarrhythmia detection algorithms using cardiac sensed event signals to determine event intervals and/or digitized cardiac electrical signals received from electrical sensing module 86 for performing morphology analysis for detecting the induced tachyarrhythmia. Upon detecting the induced tachyarrhythmia, control module 80 controls therapy delivery module 84 to deliver a therapeutic CV/DF shock to terminate the induced tachyarrhythmia. Such testing may be performed at the time of ICD implantation to verify electrode placement, tachyarrhythmia detection settings, and/or therapy control parameters used to deliver a CV/DF shock. In particular, verification that the defibrillation threshold is less than a maximum output of HV therapy module 83 may be performed by inducing a tachyarrhythmia and delivering a test shock therapy.

In other examples, control module 80 may control HV therapy module 83 to deliver a T-shock to induce ventricular tachyarrhythmia. A T-shock is an electrical pulse synchronized to the T-wave signal attendant to the repolarization phase of the ventricular myocardium, sometimes referred to as the "vulnerable period." The T-shock may be preceded by one or more entrainment pacing pulses that capture the heart to set the heart rate to facilitate synchronization of the T-shock with the T-wave signal. Control module 80 may control LV therapy module 85 to deliver the entrainment pacing pulses followed by a T-shock delivered by HV therapy module 83. In other examples, control module 80 controls HV therapy module 83 to deliver both the entrainment pulses and the T-shock.

Control parameters utilized by control module 80 for detecting cardiac rhythms and delivering electrical stimulation therapies and tachyarrhythmia induction pulses may be programmed into memory 82 via telemetry module 88. Telemetry module 88 includes a transceiver and antenna for communicating with external device 40 (shown in FIG. 1A) using RF communication as described above. Under the control of control module 80, telemetry module 88 may receive downlink telemetry from and send uplink telemetry to external device 40. In some cases, telemetry module 88 may be used to transmit and receive communication signals to/from another medical device implanted in patient 12.

Figure 6:
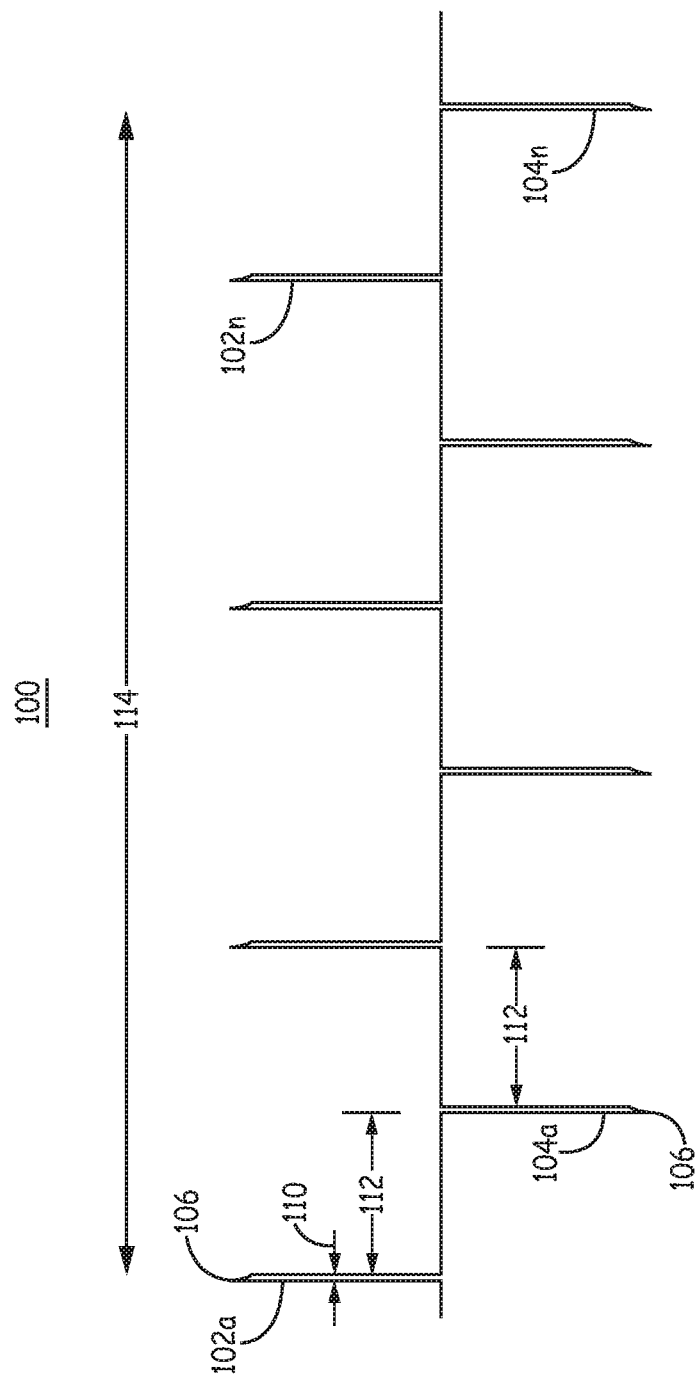
FIG. 6 is a depiction of a ventricular tachyarrhythmia induction burst that may be generated and delivered by the ICD of FIG. 5 according to one example.

FIG. 6 is a depiction of an example of a ventricular tachyarrhythmia induction burst 100 that may be generated and delivered by HV therapy module 83 of ICD 14 according to one example. Burst 100 includes alternating current pulses 102a-102n and 104a-104n. Each positive going pulse 102a-102n has a positive amplitude equal to voltage amplitude 106, and each negative going pulse 104a-104n has a negative voltage amplitude equal to voltage amplitude 106. The pulse voltage amplitude 106 greater than or equal to 10V and up to 40 V, inclusive, or may be from 10 V to 30 V in other examples. In one example, the voltage amplitude 106 of pulses 102a-102n and 104a-104n is +20 V and −20 V, respectively. Again, voltage pulse amplitude 106 may be limited to a certain minimum level, e.g., 10V or 15V or even 20V depending on the design.

Each pulse 102a-102n and 104a-104n may have a pulse width 110 of approximately 0.5 ms to 10 ms. In one example, pulse width 110 is 2 ms. The pulse burst 100 may be delivered with a pulse frequency of less than 50 Hz. In one example, burst 100 is delivered with a pulse frequency of 20 Hz. For instance, each pulse 102a-102n and 104a-104n may have a pulse width 110 of 2 ms and be separated by an inter-pulse interval 112 of 48 ms for a total pulse cycle length of 50 ms to produce a 20 Hz burst. In other examples, the inter-pulse interval 112 may be shortened to provide a 33 Hz pulse burst by using an inter-pulse interval 112 of 28 ms and pulse width 110 of 2 ms. In another example, burst 100 is delivered with a pulse frequency of 25 Hz. The inter-pulse interval is set to deliver the series of pulses 102a-n and 104a-n as a burst of pulses at a frequency that is greater than a physiological heart rate for inducing tachyarrhythmia. For example, the inter-pulse interval may be less than 100 ms to deliver a burst having a frequency that is greater than 10 Hz.

The inter-pulse interval 112 may be set based in part on the pulse amplitude 106. Charging of a HV capacitor in HV therapy module 83 to pulse amplitude 106 for delivering each pulse 102a-102n and 104a-104n occurs during the respective immediately preceding inter-pulse interval 112. The higher the voltage amplitude 106 of the positive and negative going pulses 102a-102n and 104a-104n, the longer the charge time required to reach the voltage required to generate pulses at pulse amplitude 106. As such, a higher pulse amplitude 106 may be used when the inter-pulse interval is longer, resulting in a lower frequency burst. To illustrate, the absolute value of the pulse amplitude 106 may be 20 V for a 20 Hz burst and 15 V for a 33 Hz burst. In other examples, a 20 Hz burst may have a maximum possible pulse amplitude of ±40 V and a 33 Hz burst may have a maximum possible pulse amplitude of ±20 V.

The pulse burst 100 can capture skeletal muscle in the vicinity of the electrodes used to deliver the burst. Pain or discomfort perceived by the patient generally depends on how many muscle fibers are recruited by the pulse burst 100. Decreasing the pulse amplitude 106 and/or decreasing the burst frequency can decrease the recruitment of skeletal muscle but may reduce the likelihood of inducing ventricular tachyarrhythmia. In some cases, a higher frequency burst is more tolerable to a patient because a single tetanic contraction may be induced in the skeletal muscle rather than a series of muscle twitches. Burst delivery control parameters may be selected in order to minimize or eliminate patient discomfort while maintaining a high likelihood of inducing VF.

For example, a higher voltage amplitude 106 of alternating polarity pulses 102a-102n and 104a-104n may improve success of inducing tachyarrhythmia but may require a longer inter-pulse interval 112 to charge the HV capacitor, and an overall longer burst duration 114 (greater number of pulses) may be required to induce ventricular tachyarrhythmia. The higher voltage amplitude delivered at a lower frequency for a longer period of time may be more likely to cause patient pain or discomfort. In some cases, lower voltage amplitude may be delivered at a higher frequency (shorter charge time and therefore shorter inter-pulse interval 112) and improve the likelihood of inducing tachyarrhythmia without significant patient pain or discomfort. The pulse amplitude 106, inter-pulse interval 112, and number of pulses 102a-102n and 104a-104n in burst 100 may be selected taking into consideration the trade-offs in reducing pain and successfully inducing tachyarrhythmia.

Burst 100 is shown to include 8 pulses (4 positive-going pulses 102a-102n and 4 negative-going pulses 104a-104n), however the burst duration 114 and total number of pulses delivered may vary between examples. Burst 100 may be delivered having an overall burst duration 114 of 0.5 to 2 seconds in various examples. In some instances, burst duration 114 is 1 second or less. An induction burst delivered using the techniques disclosed herein is not required to be a biphasic burst as shown in FIG. 6. In other examples, burst 100 could be monophasic instead of biphasic and all pulses could be positive-going or negative-going. For example, pulses 102a-102n may be delivered as all positive pulses at an inter-pulse interval 112 with no negative pulses, or pulses 104a-104n may be delivered as all negative pulses at inter-pulse interval 112 with no positive pulses. A monophasic or biphasic burst may include eight to twenty pulses delivered at less than 50 Hz in various examples.

Figure 7:
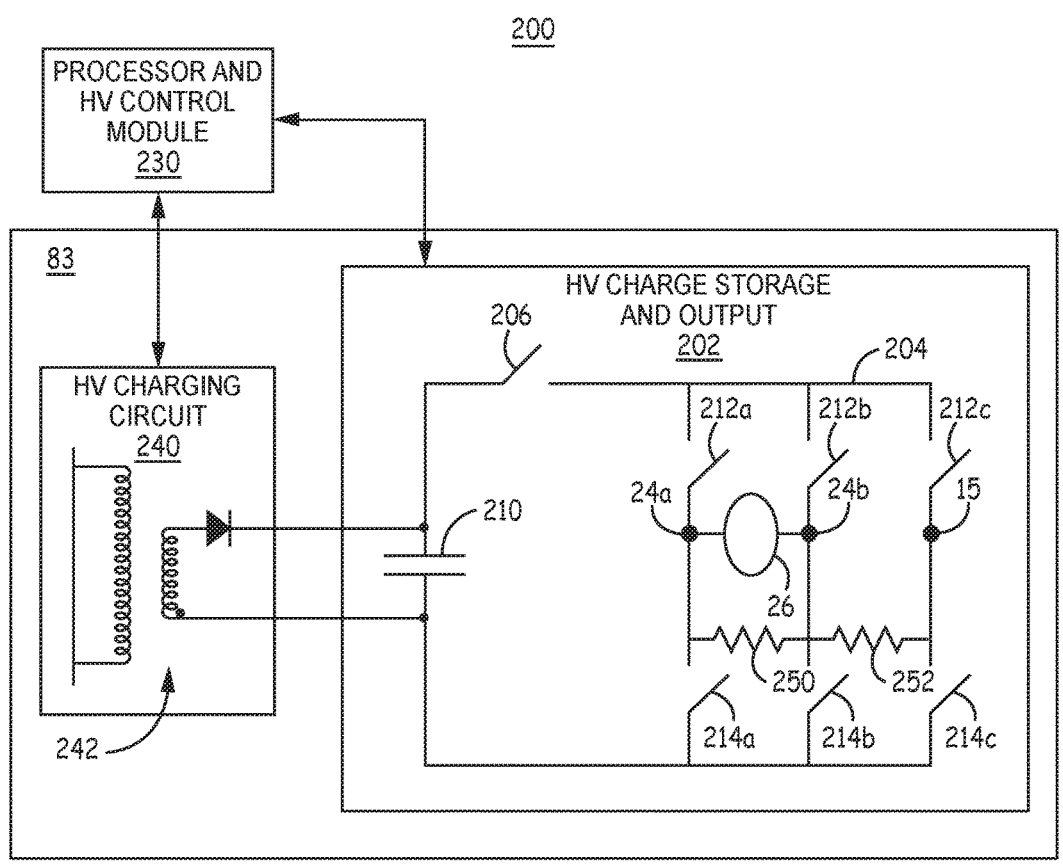
FIG. 7 is schematic diagram of a high voltage therapy module coupled to a processor and control module according to one example.

FIG. 7 is schematic diagram 200 of HV therapy module 83 coupled to a processor and HV control module 230 included in control module 80 for controlling a HV charging circuit 240 and a HV charge storage and output module 202 of HV therapy module 83. HV charge storage and output module 202 includes a HV capacitor 210 coupled to switching circuitry 204 via a pulse width control switch 206.

Switching circuitry 204 couples the HV capacitor 210 to electrodes 24a, 24b and/or housing 15 to deliver a desired HV electrical pulse to the patient's heart 26. Although only electrodes 24A and 24B and housing 15 are shown coupled to switching circuitry 204, it is to be understood that other available extra-cardiovascular electrodes, e.g., electrodes 28A, 28B and or 30 shown in the various examples of FIGS. 1A-4, may be selectively coupled to switching circuitry 204 for use in delivering tachyarrhythmia induction pulses in some examples.

HV capacitor 210 is shown as a single capacitor, but it is recognized that a bank of two or more capacitors or other energy storage devices may be used to store energy for producing electrical signals delivered to heart 26. For example a stack of capacitors having an effective capacitance of 148 microfarads may be implemented as capacitor 210. Switching circuitry 204 may be in the form of an H-bridge including switches 212a-212c and 214a-214c that are controlled by signals from processor and HV control module 230 to couple capacitor 210 to a selected electrode vector with a desired polarity when pulse width control switch 206 is in a closed or activated state.

When control module 80 determines that delivery of an electrical stimulation pulse from HV therapy module 83 is needed, pulse width control switch 206 and switching circuitry 204 are controlled by signals from processor and HV control module 230 to discharge capacitor 210 across selected electrodes 24a, 24b and/or housing 15. The selected electrodes 24a, 24b and/or housing 15 are coupled to HV capacitor 210 via opening and closing of the appropriate switches of switching circuitry 204 to produce a desired signal, which may be a monophasic, biphasic or other shaped signal. The signal may be a CV/DF shock signal for terminating a ventricular tachyarrhythmia.

For example, when a bi-phasic CV/DF shock is needed, one of switches 212a, 212b and 212c may be closed simultaneously with one of switches 214a, 214b and 214c without closing the same "a" and "b" switches across a given electrode 24a, 24b or housing 15 at the same time. To deliver a biphasic pulse using electrode 24a and housing 15, for instance, switch 212a and 214c may be closed to deliver a first phase of the biphasic pulse. Switches 212a and 214c are opened after the first phase, and switches 212c and 214a are closed to deliver the second phase of the biphasic pulse. Switches 212b and 214b remain open in this example with electrode 24b not selected in the therapy delivery vector. In other examples, electrode 24B may be included instead of electrode 24A or simultaneously activated with electrode 24A by closing switch 212b during the first phase and closing switch 214b in the second phase of the illustrative biphasic pulse.

When control module 80 determines that it is time to induce a ventricular tachyarrhythmia, processor and HV control module 230 controls switching circuitry 204 to deliver a burst of pulses, such as burst 100 of alternating polarity pulses as shown in FIG. 6, via electrodes 24a and 24b. In the case of delivering a burst of pulses to induce tachyarrhythmia, the housing 15 may be unused by holding switches 212c and 214c open. Depending on the implant location of ICD 14 and resulting electrical stimulation delivery vector between the housing 15 and one or both of electrodes 24a and 24b, greater recruitment of skeletal muscle may occur when housing 15 is included in the delivery vector. A larger volume of skeletal muscle tissue lies along a vector extending between the distal portion 25 of lead 16 and housing 15 than along a vector extending between the two electrodes 24a and 24b along lead distal portion 25. In the example configurations of FIGS. 1A-4, an induction burst may be delivered between the electrodes 24a and 24b to reduce skeletal muscle recruitment. In other electrode configurations and implant locations, the electrodes used to deliver a tachyarrhythmia induction burst may be selected to provide a delivery vector that minimizes skeletal muscle mass while directing sufficient energy to the heart 26.

An induction burst, such as burst 100 shown in FIG. 6, may be delivered between electrodes 24a and 24b by producing positive-going pulses 102a-102n by closing switch 212a and switch 214b for pulse width 110 to discharge HV capacitor 210 across electrodes 24a and 24b through heart 26 when pulse width control switch 206 is closed. The pulse width control switch 206 is opened upon expiration of a pulse width timer included in processor and HV control module 230, and electrode vector selection switches 212a and 214b are opened upon or after expiration of the pulse width 110. After a positive-going pulse, e.g., pulse 102a, HV capacitor 210 is re-charged by HV charging circuit 240 to the desired pulse amplitude 106 during the inter-pulse interval 112, when pulse width control switch 206 is opened. The negative-going pulse 104a is delivered by closing pulse width control switch 206 at the end of the inter-pulse interval and closing electrode vector selection switches 212b and 214a to deliver the next pulse 104a opposite in phase from the first pulse 102a. This process of controlling switch 206 and switches 212a, 212b,214a, and 214b to deliver alternating polarity pulses separated by an inter-pulse interval 112 continues until the burst duration 114 expires or a predetermined number of pulses 102a-102n and 104a-104n are delivered.

The HV capacitor 210 is charged to the burst pulse amplitude 106 during the inter-pulse intervals 112 so that each pulse is delivered with amplitude 106. HV charging circuit 240 receives a voltage regulated signal from power source 98. HV charging circuit 240 includes a transformer 242 to step up the battery voltage of power source 98 in order to achieve charging of capacitor 210 to a voltage that is much greater than the battery voltage. Charging of capacitor 210 by HV charging circuit 240 is performed under the control of processor and HV control module 230, which receives feedback signals from HV charge storage and output module 202 to determine when capacitor 210 is charged to a programmed voltage. A charge completion signal is passed to HV charging circuit 240 to terminate charging by processor and HV control module 230. One example of a high voltage charging circuit and its operation is generally disclosed in U.S. Pat. No. 8,195,291 (Norton, et al.), incorporated herein by reference in its entirety.

Figure 9:
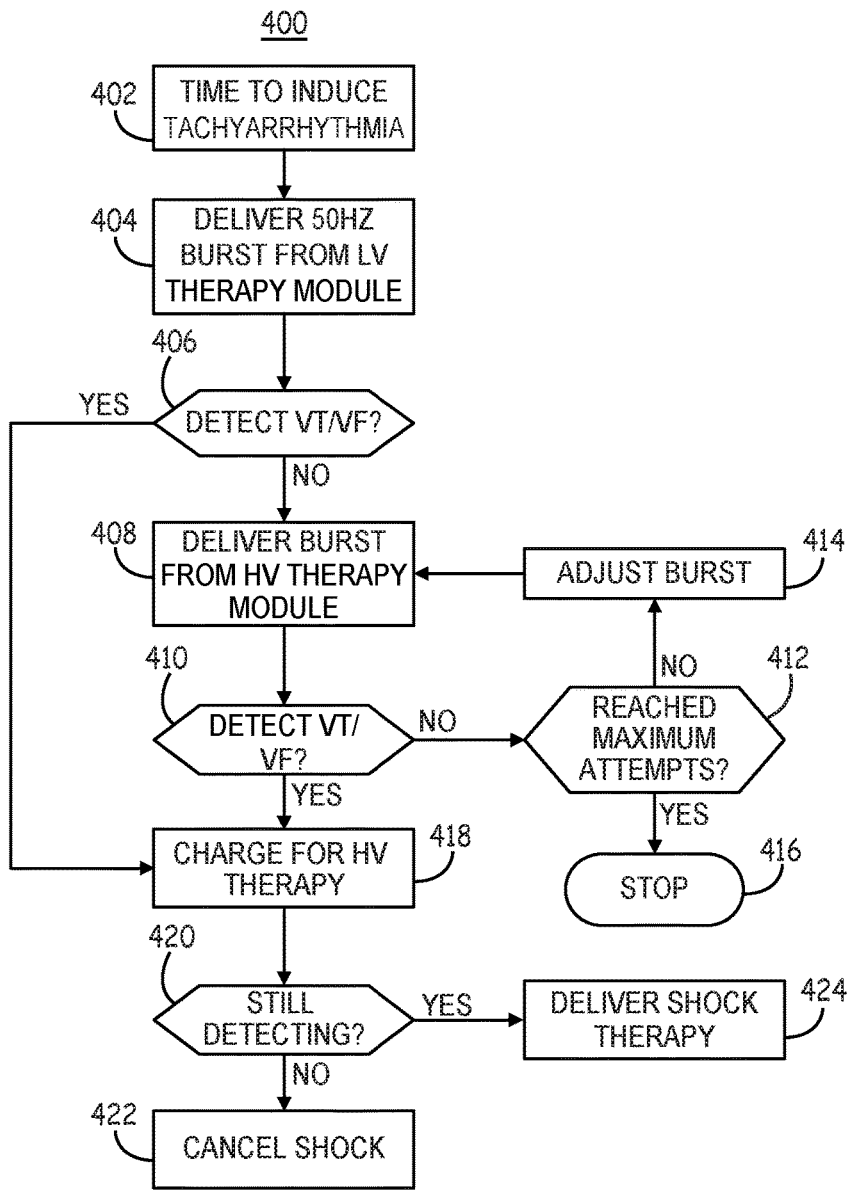
FIG. 9 is a flow chart of a method for inducing a ventricular tachyarrhythmia using the ICD and example extra-cardiovasular leads of any of FIGS. 1A-4 according to another example.

While not shown in the example of FIG. 9, in other examples electrodes 28A, 28B and 30 may be selectively coupled to HV therapy module 83 via additional switches included in switching circuitry 204 so that tachyarrhythmia induction pulses may be delivered by HV therapy module 83 using an electrode vector that includes electrodes 28A, 28B and/or 30.

HV charge storage and output module 202 may include a shunt resistance 250 in parallel to the pulse delivery load shown schematically as heart 26 when electrodes 24A and 24B are selected as the anode and cathode (or cathode and anode, respectively) of the electrode vector used to deliver induction pulses. The shunt resistance may be configured in parallel to the pulse delivery load for any selected induction pulse delivery electrode vector. For example shunt resistance 252 is shown schematically if the electrode vector used for delivering induction pulses includes electrode 24B and housing 15. Likewise the shunt resistance may be configured in parallel to the pulse delivery load when the electrode vector includes electrode 24A and housing 15.

Switches 212a-212c and switches 214a-214c may require a minimum current flow to hold them closed (i.e., ON or enabled) for passing current as capacitor 210 is discharged. This minimum current may be on the order of approximately 10 milliamps. Depending on the pulse delivery load impedance, pulse width, and other conditions, the electrical current passing through enabled switches of switches 212a-212c and 214a-214c may fall below the minimum current required to keep the switches closed as capacitor 210 is discharged across a selected electrode vector. If the current passing through a respective switch falls below the minimum current required to keep the switch closed before the pulse width expires, the switch may open (or become disabled) causing premature truncation of the electrical stimulation pulse, which could render the pulses being delivered to induce tachyarrhythmia ineffective. As such, a minimum pulse voltage amplitude may be set for delivering induction burst pulses by HV therapy module 83 or entrainment pulses prior to a T-wave shock delivered by the HV therapy module 83 in order to reduce the likelihood of the electrical current produced during capacitor discharge falling below the minimum current required to maintain a stable state of enabled switches of switching circuitry 204 during a programmed induction pulse width.

The shunt resistance 250 or 252 may be a variable resistance that is set to match an electrode vector impedance so that the load across heart 26 using a selected electrode vector matches the shunt resistance. In this way, current through the switching circuitry 204 may be maintained at or above a minimum current required to maintain a stable state of enabled switches of switching circuitry 204 during the pacing pulse. If the shunt resistance 250 is higher than the electrode vector impedance across heart 26, the electrical current applied to selected switches of switching circuitry 204 may fall below the minimum required to maintain the enabled state of the selected switches for a full duration of an electrical stimulation pulse included in an induction sequence, which may be a burst pulse or an entrainment pulse leading up to a T-wave shock.

If the shunt resistance 250 or 252 is lower than the electrode vector impedance, current produced by discharging capacitor 210 may be shunted away from the pulse delivery load, e.g., the load of the electrode vector between electrodes 24a and 24b and heart 26, resulting in less energy delivered to heart 26, which may result in loss of capture by the induction pulses and failure to induce a tachyarrhythmia. Accordingly, processor and HV therapy control module 230 may be configured to control therapy delivery module 84 to retrieve an electrode vector impedance measurement, e.g., by applying a known current across the selected electrode vector and determining the resulting voltage from which the electrode vector impedance may be determined. Processor and HV therapy control module 230 may set the variable shunt resistance 250 (or 252) to match the electrode vector impedance.

Since the range of electrode vector load impedances and stimulation pulse voltage amplitudes may vary between patients and over time, a variable shunt resistance may be provided to enable selection of the appropriate resistance for shunting the required current through the switching circuitry 204. It is contemplated, however, that in some examples a fixed resistance shunt may be provided. For example, the resistance needed to shunt current to the switching circuitry 204 when the electrode vector impedance is high may still shunt some current to the switching circuitry 204 when the electrode vector impedance is relatively lower. An optimal value for a fixed resistance shunt may be determined based on empirical data, e.g., typical electrode vector impedances and pulse voltage amplitudes used clinically.

When control module 80 determines that an induction burst is to be delivered, processor and HV control module 230, controls HV charging circuit 240 to charge capacitor 210 to the burst pulse amplitude voltage 106 during inter-pulse intervals 112 using necessary timers or clock signals to enable and disable charging at appropriate times. The HV capacitor 210 is not charged beyond a programmed pulse amplitude for burst delivery to avoid high voltages that cause undue pain or discomfort. For example, HV capacitor 210 may be charged to a programmed burst induction amplitude of 20 V by HV charging circuit 240 under the control of processor and HV control module 230 prior to starting the burst delivery and during each inter-pulse interval 112.

Figure 8:
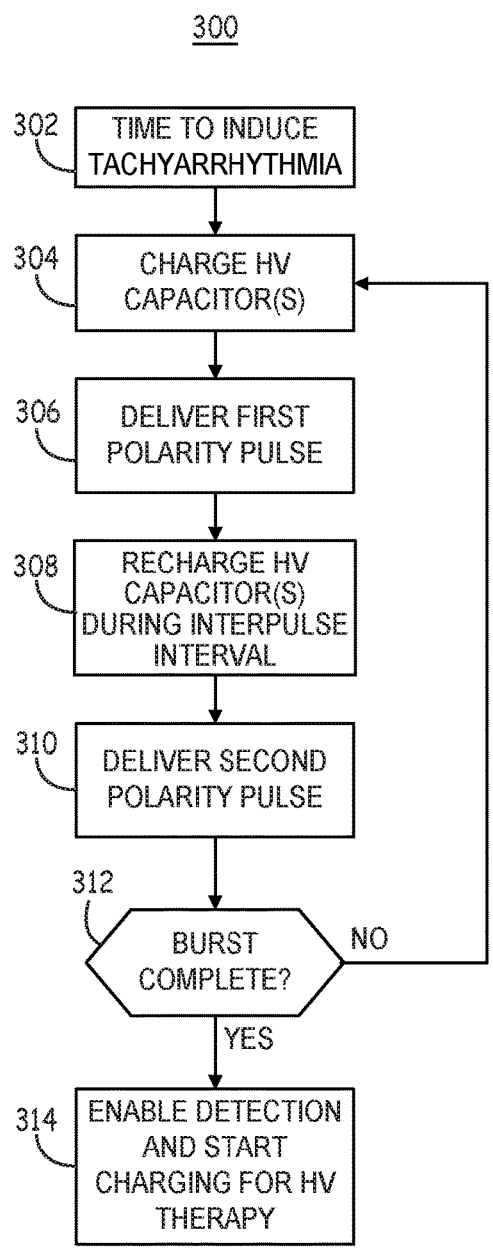
FIG. 8 is a flow chart of a method for inducing ventricular tachyarrhythmia using the ICD and example extra-cardiovasular leads of any of FIGS. 1A-4.

FIG. 8 is a flow chart 300 of a method for inducing ventricular tachyarrhythmia using extra-cardiovascular ICD system 10. At block 302, control module 80 determines if it is time to induce VT or VF. Control module 80 may initiate tachyarrhythmia induction in response to a command received from external device 40 via telemetry module 88. The tachyarrhythmia induction is initiated by controlling HV therapy module 83 to charge HV capacitor 210 to a programmed induction burst pulse amplitude 106 at block 304. At block 306, with reference to the induction burst of FIG. 6, a first polarity pulse, e.g., pulse 102a, is delivered by closing selected switches of switching circuitry 204 to discharge HV capacitor 210 across a selected burst delivery electrode vector for a predetermined pulse width 110.

The HV capacitor 210 is re-charged to the pulse amplitude 106 during the inter-pulse interval 112 at block 308. In some examples, the HV capacitor 210 may be fully re-charged to the pulse amplitude 106 during the inter-pulse interval 112. Upon expiration of the inter-pulse interval, a second polarity pulse, e.g., pulse 104a, is delivered by closing opposite switches of switching circuit 202 for pulse width 110 for coupling the selected burst delivery electrode vector in opposite polarity compared to the first polarity pulse. It is recognized, however, that in some examples, the HV capacitor 210 may not reach the full charge at the programmed pulse amplitude 106 before the inter-pulse interval 112 expires when a high burst frequency is used. The next pulse may be delivered at block 310 at the expiration of the inter-pulse interval 112 using the charge available.

If the tachyarrhythmia induction burst is not complete after delivering the second polarity pulse at block 310, as determined at block 312, the HV therapy module 83 repeats the cycle of delivering alternating current pulses at blocks 304 through 310 until control module 80 determines that the burst is complete at block 312. For example, control module 80 may include a burst duration timer or a burst pulse counter for determining if burst duration 114 has expired or if a predetermined number of pulses has been reached at block 312. If the burst is complete, control module 80 proceeds with performing tachyarrhythmia detection algorithm(s) for detecting the induced tachyarrhythmia at block 314.

As mentioned previously, alternating polarity pulses is not necessarily required in delivering a burst of pulses by HV therapy module 83. In some cases, switching circuitry 204 is controlled by processor and HV control module 230 to provide monophasic pulses in the induction burst.

Charging of HV capacitor 210 may begin during the tachyarrhythmia detection algorithm(s) performed at block 314 to provide a cardioversion/defibrillation shock upon detection of an induced ventricular tachyarrhythmia. In other examples, charging of HV capacitor 210 may begin upon detecting an induced tachyarrhythmia. The cardioversion/defibrillation shock may be delivered at a test energy in order to verify successful cardioversion/defibrillation. In some cases, the process of flow chart 300 may be performed more than once in order to determine a defibrillation threshold. In other cases, a single successful defibrillation test may be adequate for verifying the performance of ICD system 10. Clinical practice may include delivering a back-up shock therapy using an external defibrillator if the ICD 14 does not successfully terminate the induced tachyarrhythmia.

FIG. 9 is a flow chart 400 of a method for inducing a ventricular tachyarrhythmia using ICD system 10 according to another example. When control module 80 determines that it is time to induce a tachyarrhythmia at block 402, e.g., in response to a command received from external device 40, control module 80 may first control LV therapy module 85 to deliver a low-voltage, high frequency burst at block 404 using a LV capacitor typically used for delivering pacing pulses and included in LV therapy module 85. In one example, a 10 microfarad (or larger) holding capacitor may be included in LV therapy module 85, which may be charged to up to 8 V in some examples for delivering a 50 Hz burst using a burst delivery electrode vector selected from electrodes 24a, 24b, 28a, 28b, 30 and/or housing 15. Depending on the size of the capacitor(s) included in LV therapy module 85, a higher voltage amplitude may be possible, e.g., up to 10 V or up to 18 V.

Charging of a LV capacitor included in LV therapy module 85 may be performed under the control of a state machine included in control module 80 using a multiple of the direct battery signal from power supply 98 e.g., 4× the battery signal, without requiring the use of a transformer. Charging of the low-voltage capacitors may be more rapid than charging HV capacitor 210 allowing a higher burst frequency of 50 Hz to be delivered. In some patients, this low-voltage, e.g., less than 10 V or less than 20 V, 50 Hz burst delivered by LV therapy module 85 may be adequate to induce tachyarrhythmia using extra-cardiovascular electrodes 24A, 24B, 28a, 28b and/or 30.

At block 406, control module 80 performs VT/VF detection algorithms to detect an induced tachyarrhythmia. If VT or VF is detected, control module 80 may advance to block 418 to charge the HV capacitor 210 for shock delivery to terminate the induced tachyarrhythmia. As described above, the HV capacitor 210 is charged to a voltage amplitude corresponding to a programmed test shock energy to verify successful termination of the induced tachyarrhythmia using the programmed shock energy and current implant location of lead 16. The voltage amplitude corresponding to a therapeutic shock energy to be delivered as a test shock is much greater than the voltage amplitude of the series of pulses in the burst delivered to induce tachyarrhythmia. Upon charge completion, control module 80 may verify whether VF (or a shockable fast VT) is still being detected at block 420. If so, the test shock is delivered at block 424. If the shockable rhythm is not still being detected at block 420, the test shock may be cancelled at block 422.

If VT/VF is not detected at block 406, after the 50 Hz burst delivered by LV therapy module 85, the control module 80 controls HV therapy module 83 to deliver a higher-voltage, lower frequency burst using the switching circuitry 204. A higher voltage may be required to induce tachyarrhythmia using the extra-cardiovascular electrodes than the maximum pulse voltage amplitude available using the LV pacing capacitor(s) included in LV therapy module 85. As such, a burst having higher voltage pulses, which may require a lower burst frequency to provide adequate inter-pulse charge time of the HV capacitor 210, is delivered using the HV therapy module 83. At block 408, an induction burst, such as burst 100 shown in FIG. 6, is delivered using the methods described in conjunction with FIGS. 6, 7 and 8.

After delivering the induction burst using HV therapy module 83, control module 80 performs tachyarrhythmia detection at block 410. If an induced tachyarrhythmia is detected at block 410, control module 80 controls HV therapy module 83 to begin charging HV capacitor 210 at block 418 to prepare for shock delivery. In some examples, HV capacitor charging may begin as soon as the induction burst delivery is complete or during the tachyarrhythmia detection algorithm. If a shockable rhythm is still being detected at block 420 after the HV capacitor 210 is fully charged to a high voltage for shock delivery, e.g., for delivering a shock of 10 Joules or more, the test shock therapy is delivered at block 424. Otherwise the shock is cancelled at block 422. It is recognized that HV capacitor 210 is generally charged to a higher voltage for therapeutic shock delivery than for tachyarrhythmia induction pulses delivered in a series of burst pulses.

In some examples, if VF is not detected at block 410 after the first induction burst is delivered at block 408 using the HV therapy module 83, additional induction attempts may be made up to a maximum number of attempts. If a maximum number of induction attempts has been reached as determined at block 412, which may be a single induction attempt using the HV therapy module 83 to deliver a higher voltage burst (with or without attempting a preceding lower voltage burst using the LV therapy module 85), the induction process may be terminated at block 416.

If additional attempts are available, one or more control parameters used to control the induction burst delivery by HV therapy module 83 may be adjusted at block 414. For example, the pulse amplitude 106 may be increased, the pulse width 110 may be increased, the number of pulses or total pulse burst duration 114 may be increased, burst frequency may be increased by decreasing the inter-pulse interval 112, and/or the burst delivery electrode vector may be changed if additional electrodes or electrode combinations are available (depending on the particular lead and electrode configuration being used).

A burst may be delivered from HV therapy module 83 using the adjusted burst control parameter(s) at block 408. This process may continue until VT or VF is induced as detected at block 410 or until a maximum number of induction attempts is reached at block 412. One or more induction attempts using HV therapy module 83 may be made without first attempting induction using the LV therapy module 85. Once a maximum number of induction attempts is reached using a burst of pulses, ICD 14 may be configured to attempt delivering entrainment pulses followed by a T-shock as described below in conjunction with FIG. 11. It is recognized that clinical practice may include using an external device to induce a tachyarrhythmia if induction attempts by ICD 14 fail to induce the tachyarrhythmia. Furthermore, an external defibrillator may be used to provide a back-up shock therapy to terminate an induced tachyarrhythmia.

Figure 10:
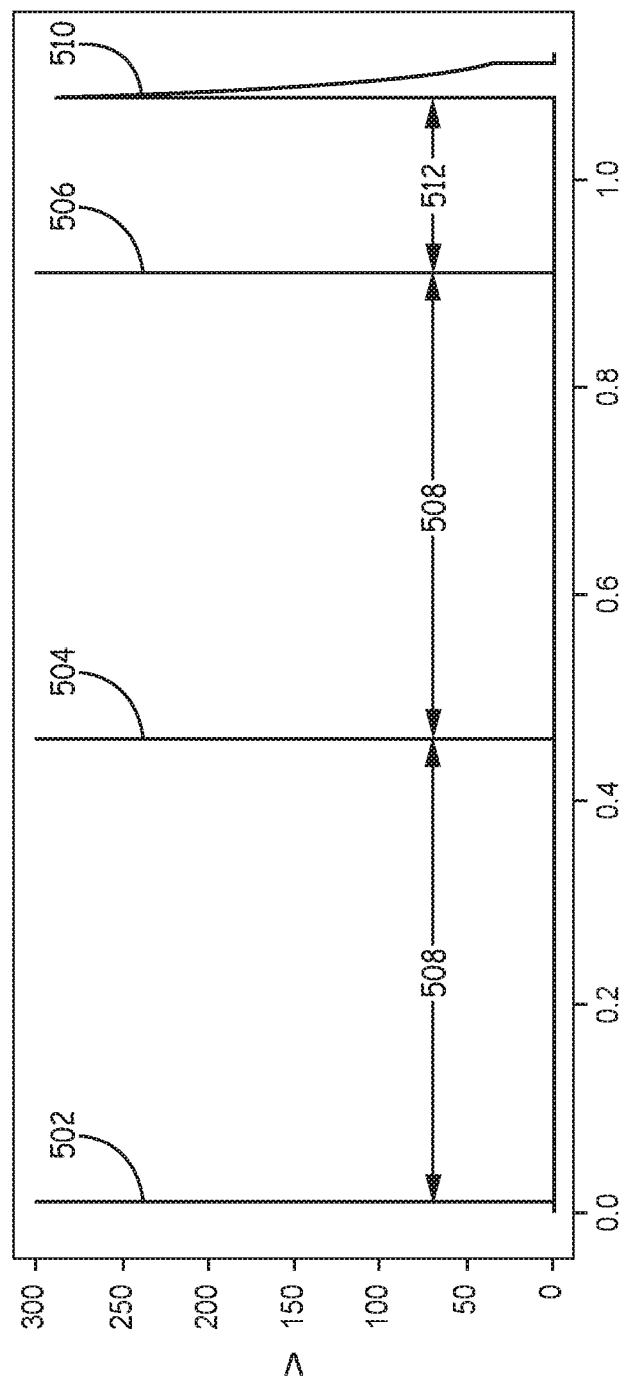
FIG. 10 is a conceptual diagram of entrainment pulses and a T-shock that may be delivered by the ICD system of FIGS. 1A-4 according to another example for inducing tachyarrhythmia.

FIG. 10 is a conceptual diagram of a series of pulses delivered for inducing tachyarrhythmia including entrainment pulses and a T-shock that may be delivered by ICD system 10 according to another example for inducing tachyarrhythmia. In this example, entrainment pulses 502, 504 and 506 are delivered to capture the heart and control the heart rate prior to delivery of T-shock 510. In other examples, sensing of intrinsic R-waves by electrical sensing module 86 may be used for synchronizing T-shock 510 with an intrinsic T-wave.

Control module 80 may control HV therapy module 83 to deliver both the entrainment pulses 502, 504 and 506 and T-shock 510. While three entrainment pulses 502, 504 and 506 are shown, it is recognized that less than three or more than three entrainment pulses may be delivered. Entrainment pulses are delivered at a rate that is greater than the patient's intrinsic heart rate, e.g., 10 to 40 pulses per minute faster than the intrinsic heart rate which may be at a rate of 100 pulses per minute or more. As such, the inter-pulse interval 508 separating the entrainment pulses 502, 504, and 506 may be an overdrive pacing interval of 600 ms or less. In the example shown, entrainment pulses 502, 504 and 506 are delivered at 130 pulses per minute at approximately 460 ms inter-pulse intervals 508.

Entrainment pulses 502, 504, and 506 may be delivered having a pulse width of 0.2 ms and a high pulse amplitude to ensure capture of the heart. In the example shown, entrainment pulses 502, 504, and 506 have a pulse amplitude of 300 volts. In other examples, a lower pulse amplitude and/or longer pulse width may be used. The pulse amplitude and pulse width selected for delivering entrainment pulses 502, 504 and 506 may be based on pacing capture thresholds determined for the individual patient or based on clinical data.

In some examples, entrainment pulses 502, 504 and 506 are delivered by the HV therapy module 83 using the variable shunt resistance 250/252 shown in FIG. 7 for passing at least a minimum current to switching circuitry 204 required for activating switches selected from switches 212a-212c and 214a-214c to enable delivery of entrainment or induction burst pulses at a relatively low voltage amplitude. Such techniques are generally disclosed in the above-incorporated provisional U.S. Pat. Application 62/262,499 and the corresponding U.S. patent application Ser. No. 15/367,516, filed on the same day herewith. For example, a variable shunt resistance may be applied in parallel to the pacing load to maintain current through switching circuitry 204 to hold the switches in an enabled or closed state when a relatively low pulse amplitude, e.g., less than 40 V, is used to deliver entrainment pulses 502, 504 and 506. A longer pulse width and lower amplitude pulse may be delivered for capturing heart 26 with high confidence prior to T-shock delivery in some patients.

Entrainment pulses 502, 504, and 506 may be delivered from HV therapy module 83 via defibrillation electrodes 24A and 24B (or 24A" and 24B") carried by lead 16. In other examples, other pacing electrode vectors may be selected for delivering entrainment pulses 502, 504, and 506. While the pulses 502, 504 and 506 and T-shock 510 are shown as monophasic pulses in FIG. 10, it is to be understood that in other examples the T-shock induction techniques disclosed herein may include delivery of biphasic pulses, which may be balanced biphasic pulses.

Processor and HV control module 230 controls HV therapy module 83 to charge capacitor 210 to a voltage for delivering a programmed T-shock energy, e.g., 10 Joules. T-shock 510 is delivered for a predetermined pulse width 514, e.g., 32 ms. T-shock 510 is delivered at an R-T time interval 512 following the last entrainment pulse 506. The R-T time interval 512 corresponds to an expected time from the pacing pulse 506 to the T-wave of the patient's ECG signal. For instance, when entrainment pulses 502, 504 and 506 are delivered at 130 pulses per minute, T-shock 510 may be delivered at an R-T time interval 512 of 170 ms after the last entrainment pulse 506. The R-T time interval 512 may be adjusted as needed for different rates of entrainment pulses or according to the patient's intrinsic heart rate when entrainment pulses are not used.

T-shock 510 may be delivered using any combination of defibrillation electrodes 24A (or 24A'), 24B (or 24B') and housing 15. In one example, T-shock 510 is delivered using housing 15 as an active can electrode and the proximal defibrillation electrode 24B (or 24B') of lead 16 as the return electrode. In other examples, T-shock 510 may be delivered between electrodes 24A and 24B (or 24A' and 24B') or between housing 15 and distal defibrillation electrode 24A (or 24A').

In other examples, control module 80 may control LV therapy module 85 to deliver entrainment pulses 502, 504 or 506. For example, entrainment pulses 502, 504 and 506 may be low-voltage, composite pacing pulses comprising a series of fused individual pulses delivered by LV therapy module 85 according to the techniques generally disclosed in U.S. Patent Application 62/262,412 and the corresponding U.S. patent application Ser. No. 15/368,197, filed on the same day herewith), incorporated herein by reference in its entirety.

Figure 11:
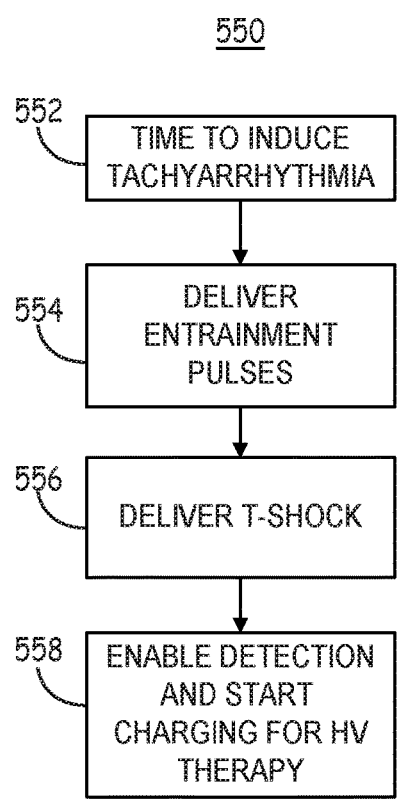
FIG. 11 is a flow chart of a method for inducing tachyarrhythmia by the ICD system of FIGS. 1A-4 according to another example.

FIG. 11 is a flow chart 550 of a method for inducing tachyarrhythmia by ICD system 10 according to another example. The method of flow chart 550 may be performed as an initial induction attempt or automatically in response to failure to induce tachyarrhythmia by a burst of pulses, e.g., according to the methods of FIG. 9. When control module 80 determines it is time to induce tachyarrhythmia at block 552, e.g., in response to a user command received from external device 40, control module 80 controls therapy delivery module 82 to deliver entrainment pulses at block 554. In one example, processor and HV control module 230 controls charging of capacitor 210 to a programmed pacing pulse amplitude for delivering entrainment pulses at a programmed rate and pulse width. Top-off charging may be enabled for charging capacitor 210 up to one second prior to initiating the entrainment pulses. The entrainment pulses may be high amplitude, relatively short duration pulses, e.g., 40 V or more and up to 1 ms in pulse width. In the example shown in FIG. 10, entrainment pulses are 300 V in amplitude and 0.2 ms in pulse width. These high amplitude entrainment pulses may be delivered between defibrillation electrodes 24A and 24B (or 24A' and 24B' of FIG. 4) in some examples.

In other examples, a relatively low voltage pulse, e.g., 40 V or less or 20 V or less, may be delivered by HV therapy module 83 using a relatively longer pulse width, e.g., greater than 1 ms and up to 10 ms in pulse width, using the techniques generally disclosed in the above-incorporated U.S. Patent Application 62/262,499 and the corresponding U.S. patent application Ser. No. 15/367,516, filed on the same day herewith. When a relatively lower voltage pulse amplitude and longer pulse width are used, control of the variable shunt resistance 250/252 may be performed to maintain an active state of selected switches of switching circuitry 204. In either case, however, HV capacitor 210 is discharged through switching circuitry 204 for delivering the entrainment pulses.

In one example, the LV therapy module 85 delivers entrainment pulses via one of electrodes 28A or 28B as the cathode and the housing 15 as the return anode. The HV therapy module 83 may deliver entrainment pulses via the defibrillation electrodes 24A and 24B, one serving as the anode and the other as the cathode, or between one of the defibrillation electrodes 24A or 24B paired with the housing 15. The delivery of pulses in a burst or as entrainment pacing pulses by the LV therapy module 85 or the HV therapy module 83 are not limited for use with a particular pacing electrode vector. The pacing electrode vectors used by the LV therapy module 85 and the HV therapy module 83 may be selected based on individual patient need and the particular lead and electrode configuration being used and its placement in the patient's body.

In still other examples, control module 80 controls LV therapy module 85 to deliver the entrainment pulses at block 554. Individual pacing pulses delivered up to a maximum pulse amplitude and/or maximum pulse width available from LV therapy module 85 may be adequate for capturing the patient's heart and controlling the heart rate for T-shock synchronization. For example, LV therapy module 85 may be capable of delivering a single-pulse pacing pulse of up to 8 V, 10 V or 20 V in some examples. The maximum pulse width may be up to and including 2 ms in some examples. As such, a series of two or more entrainment pulses may be delivered as single-pulse pacing pulses at or near the maximum available pulse amplitude and/or pulse width.

In yet another example, control module 80 may control LV therapy module 85 to deliver each entrainment pulse as a composite pacing pulse comprising two or more individual pulses delivered within the composite pacing pulse width to cause a single evoked response to each entrainment pulse. Entrainment pulses may be delivered as composite pacing pulses delivered according to the techniques generally disclosed in the above-incorporated U.S. Pat. Application 62/262,412 and the corresponding U.S. patent application Ser. No. 15/368,197, filed on the same day herewith. The method used to deliver entrainment pulses by LV therapy module 85 or HV therapy module 83 and associated control parameters, e.g., pulse amplitude, pulse width, pulse rate, and pacing electrode vector selected from the available electrodes 24A (or 24A'), 24B (or 24B'), 28A, 28B, and 30 (when present) may be programmable.

At block 556, processor and HV control module 83 controls HV therapy module 83 to deliver a T-shock. As described above, the T-shock is a high energy pulse delivered at a T-shock interval following the last entrainment pulse. The T-shock is generally more than 1 Joule and may be 10 Joules or more. The T-shock is delivered using an electrode vector from the ICD housing 15 to the inferior defibrillation electrode, e.g., defibrillation electrode 24B as shown in FIGS. 1A-4, in some examples. The control parameters used to deliver the T-shock, including the electrode vector and shock pulse energy, may be programmable. The entrainment pulses and the T-shock may be delivered by HV therapy module 83 using the same electrode vector in some examples. In other examples, the entrainment pulses may be delivered by HV therapy module using different electrode vectors. For example, high-voltage entrainment pulses may be delivered via an electrode vector between electrodes 24A and 24B and the T-shock may be delivered via an electrode vector between housing 15 and electrode 24A or electrode 24B.

Control module 80 performs tachyarrhythmia detection at block 558 after T-shock delivery and may immediately begin charging HV capacitor 210 for delivering a shock therapy to terminate an induced tachyarrhythmia. One or more tachyarrhythmia induction attempts may be made using the T-shock induction methods described in conjunction with FIGS. 10 and 11 to test ICD system 10 performance. In some examples, the method of FIG. 11 and the methods described in conjunction with the flow chart 400 of FIG. 9 may be combined. For example, if a less aggressive induction technique such as a 50 HZ burst delivered by LV therapy module 85 and/or a higher voltage, lower frequency burst (less than 50 Hz) delivered by HV therapy module 83 fail to induce tachyarrhythmia, and a maximum number of induction attempts has not been reached (block 412, FIG. 9), the T-shock induction technique of FIG. 11 may be attempted one or more times until a maximum number of induction attempts has been reached.

Figure 12:
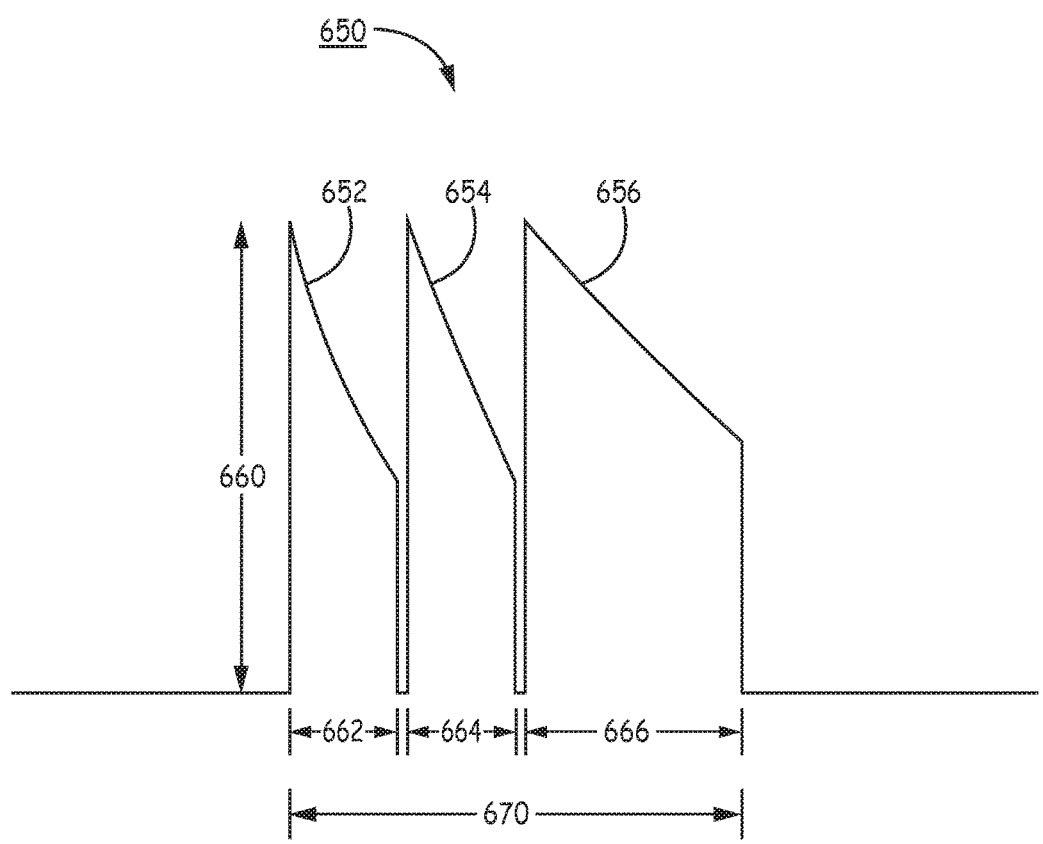
FIG. 12 is a conceptual diagram of one example of a composite pacing pulse that may be delivered as a part of a tachyarrhythmia induction sequence.

FIG. 12 is a conceptual diagram of one example of a composite pacing pulse 650 that may be delivered by LV therapy module 85 as a part of a tachyarrhythmia induction sequence. For example, composite pacing pulse 650 may be a pacing entrainment pulse delivered by LV therapy module 85 prior to a T-shock delivered by HV therapy module 83. In another example, composite pacing pulse 650 may be delivered as one pulse of a burst of pulses, e.g., a 50 Hz burst, delivered by LV therapy module 85 for inducing tachyarrhythmia using extra-cardiovascular electrodes.

Composite pacing pulse 650 includes multiple individual pulses 652, 654 and 656 delivered sequentially so that they are fused in time during the composite pulse width 670. Each individual pulse 652, 654 and 656 may have an individual pulse energy that is less than a pacing capture threshold of the heart. The individual pulse energies are delivered in fused succession, however, to accumulate delivered energy within composite pulse width 670 to provide a total composite pulse energy that is greater than the pacing capture threshold of the patient's heart.

In this example, individual pulses 652, 654 and 656 have the same polarity and peak pulse voltage amplitude 660 but may have differing pulse widths. Pulse 652 may be delivered by discharging a first holding capacitor included in LV therapy module 85 across an output capacitor on an output line of the LV therapy module 85 for an individual pulse width 662. Pulse 654 may be delivered by discharging a second holding capacitor 618 across a second output capacitor to the same output line of LV therapy module 85 for individual pulse width 664. Each of pulses 652 and 654 may be 2 ms in pulse width 662 and 664, respectively.

The last individual pulse 656 has a pulse width 666 that is longer than pulse widths 662 and 664 and may be delivered using a larger effective capacitance than the capacitance used to deliver pulses 652 and 654. For example two parallel holding capacitors included in LV therapy module 85 may be discharged simultaneously across an electrode vector via a respective output capacitor for the individual pulse width 666. The pulse width 666 may be set to 4 ms, for example, longer than pulse widths 662 and 664, because of the higher effective capacitance of the parallel holding capacitors which provides a slower decay rate of pulse 656. The total composite pacing pulse width 670 is 8 ms in this example. It is recognized that in other examples, each of the individual pulses 652, 654 and 656 may have the same or differing individual pulse widths and composite pacing pulse 670 may include two or more individual fused pulses.

The leading pulse amplitude 660 of each pulse 652, 654 and 656 may be programmable to a range of pulse amplitudes, e.g., 1 V, 2 V, 4 V, 6 V, 8 V or 10 V. The pulse voltage amplitude 660 may be selected to be greater than the pacing amplitude capture threshold when the composite pulse width 670 is 8 ms. Each holding capacitor or combination of parallel holding capacitors are charged to the pulse voltage amplitude 660 prior to delivering each respective pulse with the leading pulse voltage amplitude 660. A non-zero gap between each pulse 652, 654 and 656 may occur due to limitations of the electronics, but pulses 652, 654 and 656 are delivered close enough in time to provide a cumulative delivered pulse energy within the composite pacing pulse width 670 that is greater than the pacing capture threshold even when each pulse 652, 654 and 656 individually have a pulse energy that is less than the pacing capture threshold of the patient's heart.

In other examples, longer pulse 656 may be delivered first with one or more shorter pulses 652 and 654 following, or longer pulse 656 may be delivered between shorter pulses 652 and 654. It is recognized that numerous combinations of individual pulse number, individual pulse widths and individual pulse sequences can be conceived for delivering a composite pacing pulse utilizing the same or differing effective capacitances for each individual pulse selected from a capacitor array included in LV therapy module 85.

Negative-going recharge pulses are not shown in FIG. 12 but it is to be understood that composite pacing pulse 650 may include a negative-going portion following the positive composite pulse shown in FIG. 12 due to the passive discharge of the output capacitor that may have charged during the actively driven pulses 652, 654, and 656. Other examples of composite pacing pulses and techniques for producing composite pacing pulses by LV therapy module 85 that may be used for delivering entrainment pacing pulses prior to T-shock delivery and/or 50 Hz burst pulses for tachyarrhythmia induction as disclosed herein are described in the above-incorporated U.S. Pat. Application 62/262,412 and the corresponding U.S. patent application Ser. No. 15/368,197 filed on the same day herewith).

Each individual pulse 652, 654 and 656 may be delivered across the selected electrode vector having the same polarity (positive-going in the example shown) by sequentially coupling different capacitance elements (a single capacitor or a combination of two or more capacitors) across the selected electrode vector. Each of the different capacitance elements is charged to the peak voltage amplitude 660 prior to being coupled across the electrode vector to begin discharging. In some examples, the same capacitor or combination of capacitors may not be used to deliver two consecutive individual pulses, e.g., pulses 652 and 654, since charging of the capacitor (or combination of capacitors) to the peak voltage amplitude 66 occurs prior to initiating each respective one of the individual pulses 652, 654 and 656. The same capacitor or same combination of capacitors may be used to deliver two non-consecutive individual pulses by recharging the same capacitor or combination of capacitors to the peak voltage amplitude 660 during the intervening one or more individual pulses.

Each individual pulses 652, 654 and 656 is shown to have the same peak voltage amplitude 660 in FIG. 12. The peak voltage amplitude 660 may be the maximum voltage amplitude available from the LV therapy module 85 or a maximum voltage amplitude tolerable by the patient. The total pulse energy of the composite pacing pulse 650 may be controlled by setting the individual pulse number and individual pulse width of pulses 652, 654 and 656 to define the total pulse width 670. It is contemplated, however, that one capacitor (or combination of capacitors) that is discharged to deliver one of the individual pulses 652, 654 and 656 may be charged to a different voltage than another capacitor (or combination of capacitors) used to deliver a different one of the individual pulses. As a result, the individual pulses 652, 654 and 656 may have different peak voltage amplitudes (and/or polarity) in some instances. Individual pulses 652, 654 and 656, however, are generated by switching out a first discharging capacitor (or combination of capacitors) and switching in a next capacitor (or combination of capacitors) that is(are) charged to the desired peak voltage amplitude of the next individual pulse. A first individual pulse is thereby terminated by stopping discharging of the first capacitor(s), and the next individual pulse is started by starting discharging of the next capacitor(s).

Composite pacing pulses, delivered by the LV therapy module 85, having an 8 V amplitude and 8 ms pulse width may be in the range of 0.5 to 1.3 milliJoules for a range of electrode vector impedances of 400 to 1000 ohms. In contrast, pacing pulses delivered using endocardial electrodes or epicardial electrodes may be on the order of microJoules, e.g., 2 microJoules to 5 microJoules for a typical endocardial pacing pulse that is 2V in amplitude, 0.5 ms in pulse width and applied across a pacing electrode vector impedance of 400 to 1000 ohms.

Figure 13:
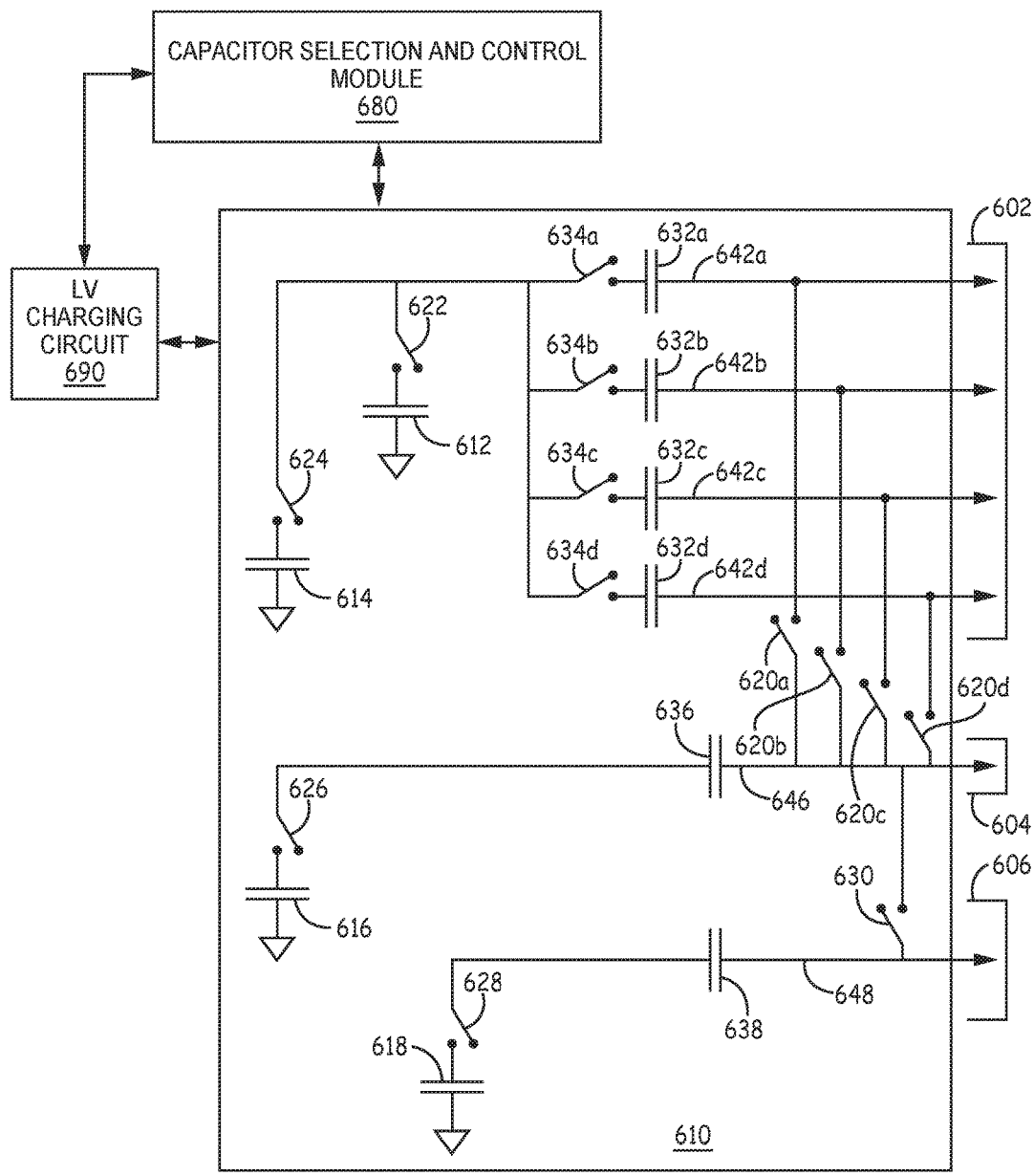
FIG. 13 is a conceptual diagram of one example of a low voltage therapy module that may be controlled to deliver electrical stimulation pulses for tachyarrhythmia induction in some examples.

FIG. 13 is a conceptual diagram of LV therapy module 85 according to one example. LV therapy module 85 may include a capacitor array 610, a capacitor selection and control module 680, and a LV charging circuit 690. Capacitor array 610 may include multiple holding capacitors 612, 614, 616 and 618 that can each be charged by LV charging circuit 690 to a programmed pulse amplitude. The holding capacitors 612, 614, 616 and 618 are coupled to a respective output capacitor 632a-632d (collectively 632), 636, or 638 via respective switches 622, 624, 626, and 628 to deliver low-voltage pulses, up to 10 V in amplitude or up to 20 V in amplitude in some examples. Each of holding capacitors 612, 614, 616 and 618 has a capacitance that is less than the effective capacitance of high voltage capacitor 210 of HV therapy module 83. For example each of holding capacitors 612, 614, 616 and 618 may have a capacitance of up to 6 microfarads, up to 10 microfarads, up to 20 microfarads or other selected capacitance, but all have a capacitance significantly less than the effective capacitance of high voltage capacitor 210, which may be 100 microfarads or greater, e.g., 148 microfarads.

Power source 98 (FIG. 5) may provide regulated power to LV charging circuit 690. LV charging circuit 690 may be controlled by a state machine in capacitor selection and control module 680 to charge all or selected holding capacitors 612, 614, 616 and 618 using a multiple of the battery voltage of power source 98, e.g., four times the battery voltage. LV charging circuit 690 charges capacitors 612, 614, 616 and/or 618 as needed for delivering low voltage pulses, either as single pulses or composite pulses, according to a tachyarrhythmia induction protocol.

In some examples, the LV therapy module 85 includes three output channels 602, 604 and 606. Each channel is capable of producing a single-pulse electrical stimulation pulse when a respective holding capacitor 612, 616 or 618 is discharged across an output capacitor 632, 636, or 638, respectively. Channel 602 includes a second holding capacitor 614 that may be used for in parallel with holding capacitor 612 for a higher effective capacitance. Holding capacitor 614 may be charged and discharged to deliver an individual pulse of a composite pacing pulse or charged and discharged in combination with holding capacitor 612 for delivering an individual pulse that may have a greater pulse width than when a single holding capacitor 612 or 614 is discharged by itself.

Channel 602 is shown in this example to include multiple selectable pacing output signal lines 642a-642d that may be selectively coupled to holding capacitor 612 and/or holding capacitor 614 via closure of one or more electrode selection switches 634a-634d. For example, multiple electrodes carried by lead 16 may be coupled to channel 602 and a pulse delivery electrode vector may be selected from the multiple electrodes by closing certain ones of switches 634a-634d.

Channels 604 and 606 are shown having single output signal lines 646 and 648 that are coupled to respective holding capacitors 616 and 618 via respective switches 626 and 628. In other examples, all three channels 602, 604 and 606 may be provided with a single output signal line or with multiple output signal lines to enable selection of a pulse delivery electrode vector from among multiple extra-cardiovascular electrodes coupled to ICD 14, e.g., any of electrodes 24A, 24B, 28A, 28B, and 30 of lead 16 shown in FIGS. 1A-4.

When tachyarrhythmia induction is enabled by control module 80, any one of the pacing channels 602, 604 and 606 may be used to deliver a series of single-pulse induction pulses. The single-pulse induction pulses may be included in a high frequency burst, e.g., a 50 Hz burst of pulses, or in a series of two or more entrainment pacing pulses delivered to control the heart rate for synchronization of a T-wave shock delivered by HV therapy module 83. The single-pulse induction pulses may be delivered by discharging one of the holding capacitors 612, 614, 616 or 618 across a selected pulse delivery electrode vector via a respective output capacitor 632, 636 or 638 when a respective switch 622, 624, 626 or 628 is closed. The output line 642a, 642b, 642c, or 642d used to deliver current from channel 602 may be selected via a respective electrode selection switch 634a-634d. The switches 622, 624, 626 or 628 that enable discharge of a holding capacitor 612, 614, 616, or 618, respectively, may be enabled by capacitor selection and control module 504 at the appropriate time when an electrical stimulation pulse is scheduled and the switch is maintained in an active, enabled state until the single-pulse pulse width is expired.

For example, channel 602 may be coupled to pace/sense electrode 28A, channel 604 may be coupled to pace/sense electrode 28B and channel 606 may be coupled to pace/sense electrode 30 in the electrode arrangement shown in FIGS. 1A-2C. If additional pace/sense electrodes are available, or if defibrillation electrodes 24A and 24B are also used for delivering electrical stimulation pulses by LV therapy module 85, the additional electrodes or defibrillation electrodes 24A and 24B may be coupled to an output channel, such as channel 602, to provide multiple selectable pulse delivery electrode vectors.

Control module 80 may control LV therapy module 85 to deliver composite-pulse induction pulses using two or more of the channels 602, 604 and 606 tied together by switches 620a-620d and/or 630 to enable individual pulses to be delivered across a selected pulse delivery electrode vector from a single output signal line 646. For example, control module 80 may enable composite-pulse induction pulses by activating switches 620a-620b and 630 to tie output lines 642a-642d and output line 648 to channel 604. Control module 80 controls capacitor selection and control module 680 to enable switches 622, 624, 626 and 628 (and at least one electrode selection switch 634a-634d of channel 602) in a sequential manner to couple a respective holding capacitor 612, 614, 616 or 618 to output signal line 646 to deliver a sequence of fused, individual pulses to produce a composite pacing pulse.

In various examples, depending on the lead and electrode configuration used with ICD 14, some electrode selection switches shown in FIG. 13 may not be required. Furthermore, it is recognized that less than four holding capacitors or more than four holding capacitors may be included in a capacitor array 610 for use in delivering a sequence of fused pacing pulses when composite pulses are delivered in an induction sequence.

Capacitor selection and control module 680 selects which holding capacitors 612, 614, 616 and 618 are coupled to output line 646 and in what sequence by controlling respective switches 622, 624, 626 and 628. A sequence of pulses may be delivered to produce a composite pulse by sequentially discharging holding capacitors 612, 614, 616 and 618 one at a time (or one combination at a time) across a respective output capacitor 632, 636 and 638 by sequentially enabling or closing the respective switches 622, 624, 626 and 628. For example, at least two of holding capacitors 612, 614, 616 and 618 are sequentially discharged to produce a composite pulse produced by at least two fused individual pulses. Output line 646 may be electrically coupled to a cathode electrode carried by lead 16 and a return anode electrode carried by lead 16 (or housing 15) may be coupled to ground. The cathode electrode and return anode electrode may correspond to electrodes 28A and 28B in one example, or any pulse delivery electrode vector selected from electrodes 24A, 24B, 28A, 28B, 30 and/or housing 15 shown in FIG. 1A through FIG. 4.

In some examples, a composite pulse is delivered on output line 646 by closing configuration switch 630 and at least one of configuration switches 620a to tie all channels 602, 604 and 606 to the single output line 646. The composite pulse, such as pulse 650 of FIG. 12, may be delivered by delivering a first individual pulse by discharging holding capacitor 616, a second individual pulse by discharging holding capacitor 618, and a third, longer individual pulse delivered by discharging both capacitors 612 and 614 simultaneously. The first two individual pulses may be 2.0 ms in pulse width and the third pulse may be 4.0 ms in pulse width for a composite pulse width of 8 ms. The higher capacitance of the parallel capacitors 612 and 614 allows for the third individual pulse to be longer in pulse width while maintaining a pulse amplitude that successfully captures the heart. All three individual pulses are delivered via output line 646 because output configuration switches 620 and 630 are enabled.

In other examples, selected ones of holding capacitors 612, 614, 616, and 618 are discharged sequentially. For example, to deliver a composite pulse including four individual pulses each of holding capacitors 612, 614, 616 and 618 may be discharged for 2.0 ms, one at a time in fused succession to deliver a composite pacing pulse having a pulse width of 8 ms. In other examples, the composite pacing pulse may have a pulse width of more than 8 ms or less than 8 ms, e.g., more than 2 ms and up to 12 ms or more depending on the number of individual pulses and their respective pulse widths. Each holding capacitor 612, 614, 616 and 618 is charged to the pulse voltage amplitude set by control module 80, e.g., 10 V or less, which may be based on a pacing capture threshold test. Other examples of a LV therapy module configured to deliver extra-cardiovascular pacing pulses that may be used for delivering induction pulses according to the techniques disclosed herein are generally disclosed in the above-incorporated in U.S. Pat. Application 62/262,412 and the corresponding U.S. patent application Ser. No. 15/368,197, and in U.S. Pat. Application 62/262,499 and the corresponding U.S. patent application Ser. No. 15/367,516.

Thus, methods and apparatus for inducing ventricular tachyarrhythmia using an extra-cardiovascular ICD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A device comprising:
a sensing module for acquiring a cardiac electrical signal;
a high voltage therapy module comprising a high voltage charging circuit, a high voltage capacitor, and switching circuitry configured to couple the high voltage capacitor to a plurality of electrodes; and
a control module configured to:
control the high voltage therapy module to induce a tachyarrhythmia by controlling the high voltage therapy module to:
charge the high voltage capacitor to a first voltage amplitude;
deliver a first series of pulses comprising a plurality of consecutive pulses having a first inter-pulse interval between each of the consecutive pulses to a patient's heart by enabling the switching circuitry to discharge the high voltage capacitor via an electrode vector of the plurality of electrodes;
recharge the high voltage capacitor during each of the first inter-pulse intervals between the consecutive pulses of the first series of pulses;
detect from the cardiac electrical signal if an induced tachyarrhythmia after the first series of pulses;
in response to detecting the induced tachyarrhythmia, control the high voltage therapy module to charge the high voltage capacitor to a second voltage amplitude greater than the first voltage amplitude, the second voltage amplitude corresponding to a therapeutic shock energy; and
discharge the high voltage capacitor to deliver the therapeutic shock energy to the patient's heart.

2. The device of claim 1, wherein the control circuit is configured to control the high voltage therapy module to recharge the high voltage capacitor to the first voltage amplitude during the first inter-pulse interval.

3. The device of claim 2, wherein the control module is configured to control the high voltage therapy module to deliver the first series of pulses as a burst of pulses at a frequency defined by the first inter-pulse interval, the first inter-pulse interval being less than 100 ms.

4. The device of claim 1, wherein the control module is configured to control the high voltage therapy module to deliver the first series of pulses as a burst of pulses at a frequency defined by the first inter-pulse interval, the first inter-pulse interval being less than 100 ms.

5. The device of claim 1, wherein the control module is further configured to control the high voltage therapy module to deliver the first series of pulses as a plurality of alternating polarity pulses.

6. The device of claim 1, wherein the control module is further configured to:
in response to determining that tachyarrhythmia is not induced by the first series of pulses, control the high voltage therapy module to:
deliver a second series of pulses having a second inter-pulse interval between consecutive pulses by enabling the switching circuitry to discharge the high voltage capacitor, the second inter-pulse interval different than the first inter-pulse interval of the first series of pulses; and
recharge the high voltage capacitor during the second inter-pulse interval between consecutive pulses of the second series of pulses.

7. The device of claim 6, wherein charging the high voltage capacitor during the second inter-pulse interval comprises charging the high voltage capacitor to a third voltage amplitude by the high voltage charging circuit, the third voltage amplitude different than the first voltage amplitude and less than the second voltage amplitude.

8. The device of claim 1, wherein the control module is configured to control the switching circuitry to couple the high voltage therapy module to the electrode vector and deliver the first series of pulses and the therapeutic shock energy via the electrode vector.

9. The device of claim 1, wherein the control module is further configured to:
control the therapy module to charge the high voltage capacitor to a third voltage amplitude greater than the first voltage amplitude after the first series of pulses;
discharge the high voltage capacitor charged to the third voltage amplitude after an R-T time interval following a last pulse of the first series of pulses; and
wherein determining if tachyarrhythmia is induced by the first series comprises determining if tachyarrhythmia is induced after discharging the high voltage capacitor after the R-T time interval.

10. The device of claim 9, wherein the control module is configured to control the switching circuitry to couple the high voltage therapy module to the electrode vector and deliver the first series of pulses and discharge the high voltage capacitor charged to the third voltage amplitude via the electrode vector.

11. The device of claim 1, further comprising:
a low voltage therapy module comprising a low voltage capacitor having a first capacitance,
the high voltage capacitor having a second capacitance greater than the first capacitance;
wherein the control module is configured to:
control the low voltage therapy module to deliver a burst of pulses having a second inter-pulse interval between consecutive pulses of the burst, the second inter-pulse interval less than the first inter-pulse interval;
determine from the cardiac electrical signal if tachyarrhythmia is induced by the burst of pulses delivered by the low voltage therapy module; and
control the high voltage therapy module to deliver the first series of pulses in response to tachyarrhythmia not being induced by the burst of pulses delivered by the low voltage therapy module.

12. The device of claim 11, wherein:
the low voltage therapy module comprises a plurality of capacitors each having a capacitance less than the second capacitance; and
the control module is configured to control the low voltage therapy module to deliver each of the pulses of the burst of pulses as a composite pulse comprising a sequence of at least two individual pulses delivered during a composite pulse width, each of the at least two individual pulses having an individual pulse energy less than a capture threshold of the patient's heart.

13. The device of claim 1, further comprising:
a low voltage therapy module comprising a low voltage capacitor having a first capacitance, the high voltage capacitor having second capacitance greater than the first capacitance;

wherein the control module is configured to:

in response to determining from the cardiac electrical signal that tachyarrhythmia is not induced by the first series of pulses, control the low voltage therapy module to deliver a second series of pulses;

charge the high voltage capacitor to a third voltage amplitude greater than the first voltage amplitude; and discharge the high voltage capacitor charged to the third voltage amplitude at an R-T time interval after a last pulse of the second series of pulses.

14. The device of claim 13, wherein:

the low voltage therapy module comprises a plurality of capacitors each having a capacitance less than the second capacitance; and the control module is configured to control the low voltage therapy module to deliver each of the pulses of the second series of pulses as a composite pacing pulse comprising a sequence of at least two individual pulses delivered during a composite pacing pulse width, each of the at least two individual pulses having an individual pulse energy less than a capture threshold of the patient's heart.

15. The device of claim 1, wherein at least a pair of the plurality of electrodes is carried on a lead couplable to the device and the control module is configured to control the switching circuitry to deliver the first series of pulses across the pair of electrodes.

16. The device of claim 1, further comprising a housing enclosing the high voltage therapy module and the control module;

wherein the control module controls the high voltage therapy module to:

deliver the first series of pulses via a first electrode vector comprising a first extra-cardiovascular electrode carried by lead and a second electrode carried by the lead; and deliver the therapeutic shock energy after the first series of pulses via a second electrode vector including the housing and at least one of the first electrode or the second electrode.

17. The device of claim 1, wherein the high voltage capacitor has a capacitance of at least 100 microfarads.

18. The device of claim 1, wherein the therapeutic shock energy is greater than 100 volts.

19. A method comprising:

charging a high voltage capacitor to a first voltage amplitude;

delivering a first series of pulses comprising a plurality of consecutive pulses having a first inter-pulse interval between each of the consecutive pulses to a patient's heart by discharging the high voltage capacitor via an electrode vector;

recharging the high voltage capacitor during each of the first inter-pulse intervals between the consecutive pulses of the first series of pulses;

receiving a cardiac electrical signal;

detecting from the cardiac electrical signal an induced tachyarrhythmia after the first series of pulses;

in response to detecting the induced tachyarrhythmia, charging the high voltage capacitor to a second voltage amplitude greater than the first voltage amplitude, the second voltage amplitude corresponding to a therapeutic shock energy; and discharging the high voltage capacitor to deliver the therapeutic shock energy to the patient's heart.

20. The method of claim 19, further comprising recharging the high voltage capacitor to the first voltage amplitude during the first inter-pulse interval.

21. The method of claim 19, further comprising delivering the first series of pulses as a burst of pulses at a frequency defined by the first inter-pulse interval, the first inter-pulse interval being less than 100 ms.

22. The method of claim 19, wherein delivering the first series of pulses comprises delivering a plurality of alternating polarity pulses.

* * * * *